(12) United States Patent
Manoharan et al.

(10) Patent No.: US 6,531,590 B1
(45) Date of Patent: *Mar. 11, 2003

(54) PROCESSES FOR THE SYNTHESIS OF OLIGONUCLEOTIDE COMPOUNDS

(75) Inventors: Muthiah Manoharan, Carlsbad, CA (US); Andrei Guzaev, Carlsbad, CA (US)

(73) Assignee: ISIS Pharmaceuticals, Inc., Carlsbad, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 369 days.

(21) Appl. No.: 09/066,638

(22) Filed: Apr. 24, 1998

(51) Int. Cl.$^7$ .............................. C07H 21/00
(52) U.S. Cl. .............. 536/25.34; 435/91.1; 558/70; 536/23.1; 536/24.5
(58) Field of Search .............. 536/23.1, 25, 34, 536/24.5; 435/91.1; 558/70

(56) References Cited

U.S. PATENT DOCUMENTS

| | | | |
|---|---|---|---|
| 3,687,808 A | 8/1972 | Merigan et al. | 435/19.3 |
| 4,415,732 A | 11/1983 | Caruthers et al. | 536/26.5 |
| 4,458,066 A | 7/1984 | Caruthers et al. | 536/25.34 |
| 4,500,707 A | 2/1985 | Caruthers et al. | 536/25.34 |
| 4,668,777 A | 5/1987 | Caruthers et al. | 536/26.5 |
| 4,725,677 A | 2/1988 | Köster et al. | 536/25.34 |
| 4,816,571 A | 3/1989 | Andrus et al. | 536/25.3 |
| 4,973,679 A | 11/1990 | Caruthers et al. | 536/26.71 |
| 5,132,418 A | 7/1992 | Caruthers et al. | 536/25.3 |
| RE34,069 E | 9/1992 | Köster et al. | 536/25.34 |
| 5,210,264 A | 5/1993 | Yau | 558/167 |
| 5,212,295 A | 5/1993 | Cook | 536/26.7 |
| 5,770,713 A * | 6/1998 | Imbach et al. | 536/22.1 |
| 5,955,591 A * | 9/1999 | Imbach et al. | 536/23.1 |

FOREIGN PATENT DOCUMENTS

| | | | |
|---|---|---|---|
| EP | 0 506 242 A1 | | 3/1992 |
| JP | 61-238 797 | * | 10/1986 |
| JP | 6-96590 | * | 11/1994 |
| WO | 9114696 | * | 10/1991 |
| WO | 9312132 | * | 6/1993 |
| WO | WO 94/26764 A1 | * | 11/1994 |
| WO | 9640164 | * | 12/1996 |
| WO | 9747637 | * | 12/1997 |

OTHER PUBLICATIONS

Tosquellas et al. (I). "The Pro–Oligonucleotide Approach: Solid Phase Synthesis and Preliminary Evaluation of Model Pro–Dodecathymidylates," *Nucleic Acids Research*, 26(9), 2069–2074 (May 1, 1998).*

Guzaev et al., "Synthesis of $^{14}$C–Radiolabelled Oligonucleotides with a Novel Phosphoramidite Reagent," *Bioorganic & Medicinal Chemistry Letters*, 8(9), 1123–1126 (May 5, 1998).*

Zuckerman et al., "Efficient Methods for Attachment of Thiol Specific Probes to the 3'–Ends of Synthetic Oligodeoxyribonucleotides," *Nucleic Acids Research*, 15(13), 5305–5321 (Jul. 10, 1987).*

Gupta et al., "A General Method for the Synthesis of 3'–Sulfhydryl and Phosphate Group Containing Oligonucleotides," *Nucleic Acids Research*, 19(11), 3019–3025 (Jun. 11, 1991).*

Asseline et al., "Synthesis and Physicochemical Properties of Oligonucleotides Built with Either α–L or β–L Nucleotide Units and Covalently Linked to an Acridine Derivative," *Nucleic Acids Research*, 19(15), 4067–4074 (Aug. 11, 1991).*

Wiesler et al., "Synthesis of Phosphorodithioate DNA via Sulfur–Linked, Base Labile Protecting Groups," *Journal of Organic Chemistry*, 61(13), 4272–4281 (Jun. 28, 1996).*

Mignet et al. (I), "The Pro–Oligonucleotide Approach V: Influence of the Phosphorus Atom Environment on the Hydrolysis of Enzymolabile Dinucleoside Phosphotriesters," *Bioorganic & Medicinal Chemistry Letters*, 7(7), 851–854 (Apr. 8, 1997).*

Barber et al., "The Prooligonucleotide Approach. I: Esterase–Mediated Reversibility of Dithymidine S–Alkyl–Phosphorothioates to Dithymidine Phosphorothioates," *Bioorganic & Medicinal Chemistry Letters*, 5(6), 563–568 (Mar. 16, 1995).*

Tosquellas et al. (II), "The Prooligonucleotide Approach. III: Synthesis and Reversibility of a Chimeric Phosphorodithioate Prooligonucleotide," *Bioorganic & Medicinal Chemistry Letters*, 6(4), 457–462 (Feb. 20, 1996).*

Mignet et al. (II), "Synthesis and Evaluation of Glucouronic Acid Derivatives as Alkylating Agents for the Reversible Masking of Internucleoside Groups of Antisense Oligonucleotides," *Carbohydrate Research*, 303(1), 17–24 (Aug. 25, 1997).*

Asseline et al., "Solid–Phase Synthesis of Modified Oligodeoxyribonucleotides with an Acridine Derivative or a Thiophosphate Group at their 3'End," *Tetrahedron Letters*, 30(19), 2521–2524 (1989).*

Cook, P. D., "Medicinal Chemistry Strategies for Antisense Research," Chapter 9 in *Antisense Research and Applications*, Crooke & Lebleu (eds.), CRC Press, Boca Raton, FL, 1993, only pp. 165 and 179 supplied.††*

(List continued on next page.)

Primary Examiner—Johann Richter
Assistant Examiner—Lawrence E Crane
(74) Attorney, Agent, or Firm—Woodcock Washburn LLP

(57) ABSTRACT

Methods for the preparation of oligonucleotides having bioreversible phosphate blocking groups are disclosed. The oligonucleotides are prepared utilizing amidite type chemistry wherein the bioreversible phosphorus protecting group is formed as an integral part of the amidite reagent.

19 Claims, 4 Drawing Sheets

OTHER PUBLICATIONS

Manoharan, M., "Designer Antisense Oligonucleotides: Conjugation Chemistry and Functionality Placement," Chapter 17 in *Antisense Research and Applications*, Crooke & Lebleu (eds.), CRC Press, Boca Raton, FL, 1993, only pp. 325–326 and 339 supplied.††*

Sharp, D.W.A., *The Penguin Dictionary of Chemistry*, Second Edition, Penguin Putnam, Inc., New York, NY, 1990, only p. 359 supplied.*

Alul, R.H. et al., "Oxalyl–CPG: a labile support for synthesis of sensitive oligonucleotide derivatives", *Nuc. Acid Res.*, 1991, 19, 1527–1532 (No. 7).

Bannwarth, W., "Synthesis of Oligodeoxynucleotides by the Phosphite–Triester Method Using Dimer Units and Different Phosphorous–Protecting Groups", *Helvetica Chim. Acta*, 1985, 68, 1907–1913.

Beaucage, S.L. et al., "Advances in the Synthesis of Oligonucleotides by the Phosphoramidite Approach", *Tetrahedron*, 1992, 48, 2223–2311.

Bielinska, A. et al., "Regulation of Gene Expression with Double-Stranded Phosphorothioate Oligonucleotides", *Science*, 1990, 250, 997–1000 (Nov. 16, 1990).

Cook, P.D., "Medicinal chemistry of antisense oligonucleotides—future opportunities", *Anti–Cancer Drug Design*, 1991, 6, 585–607.

Crooke, S.T. et al., "Pharmacokinetic Properties of Several Novel Oligonucleotide Analogs in mice", *J. Pharmacol. Exp. Therapeutics*, 1996, 277, 923–937 (No. 2).

Crooke, S.T. et al., "Progress in Antisense Oligonucleotide Therapeutic", *Ann. Rev. Pharmacol. Toxicol.*, 1996, 36, 107–129.

Crooke, S.T., "Nucleic Acid Therapeutics", in *Pharmaceutical Manufacturing International: The International Review of Pharmaceutical Technology Research and Development*, Sterling, London, Barnacal, P.A. (ed.), 1992, 4 pages.

Delgado, C. et al., "The Uses and Properties of PEG–Linked Proteins", *Crit. Rev. in Therapeutic Drug Carrier Sys.*, 1992, 9, 249–304 (Issue No. 3–4).

Dell'Aquila et al., "Photolabile Linker for the Solid–Phase Synthesis of Base-Sensitive Oligonucleotides", *Tetra. Lett.*, 1997, 38(30), 5289–5292.

Efimov, V.A. et al., "New efficient sulfurizing reagents for the preparation of oligodeoxyribonucleotide phosphorothioate analogues", *Nucl. Acids Res.*, 1995, 23, 4029–4033.

Englisch, U. et al., "Chemically Modified Oligonucleotides as Probes and Inhibitors", *Angew. Chem. Int. Ed. Eng.*, 1991, 30, 613–629 (No. 6, Jun. 1991).

Green and Wuts, "Protection for the Hydroxyl Group, Including 1,2– and 1,3–Diols", *Protective Groups in Organic Synthesis*, 2d Ed., John Wiley & Sons, New York, Chapter 2, 1991, 10–142.

Green and Wuts, "Protection for the Amino Group", *Protective Groups in Organic Synthesis*, 2d Ed., John Wiley & Sons, New York, Chapter 7, 1991, 309–405.

Greenberg et al., "Photochemical Cleavage of Oligonucleotides From Solid Phase Supports", *Tetra. Lett.*, 1993, 34(2), 251–254.

Holmes et al., "Model Studies for New o–Nitrobenzyl Photolabile Linkers: Substituent Effects on the Rates of Photochemical Cleavage", *J. Org. Chem.*, 1997, 62, 2370–2380 (Issue No. 8).

Iyer, R.P. et al., "The Automated Synthesis of Sulfur–Containing Oligodeoxyribonucleotides Using 3H–1,2–Benzodithiol-3–one 1,1–Dioxide as a Sulfur–Transfer Reagent", *J. Org. Chem.*, 1990, 55, 4693–4699.

Iyer, R.P. et al., "3H–1,2–Benzodithiole–3–one 1,1–Dioxide as an Improved Sulfurizing Reagent in the Solid–Phase Synthesis of Oligodeoxyribonucleoside Phosphorothioates", *J. Am. Chem. Soc.*, 1990, 112, 1253–1254.

Kamer, P.C.J. et al., "An Efficient Approach Toward the Synthesis of Phosphorothioate Diesters via the Schonberg Reaction", *Tetrahedron Letts.*, 1989, 30, 6757–6760 (Issue No. 48).

Kroschwitz, J.I., "Polynucleotides", *Concise Encyclopedia of Polymer Science and Engineering*, 1990, John Wiley & Sons, New York, 858–859.

Kumar, G. et al., "Improvements in Oligodeoxyribonucleotide Synthesis: Methyl N,N–Dialkylphosphoramidite Dimer Units for Solid Support Phosphite Methodology", *J. Org. Chem.*, 1984, 49, 4905–4912 (Issue No. 25).

Leeds, J.M. et al., "Quantitation of Phosphorothioate Oligonucleotides in Human Plasma", *Analyt. Biochem.*, 1996, 235, 36–43.

Milligan et al., "Current Concepts in Antisense Drug Design", *J. Med. Chem.*, 1993, 36(14), 1923–1937 (Jul. 9, 1993).

Miura, K. et al., "Blockwise Mechanical Synthesis of Oligonucleotides by the Phosphoramidite Method", *Chem Pharm. Bull.*, 1987, 35, 833–836 (Issue No. 2).

Ouchi, T. et al., "Synthesis and Antitumor Activity of Poly(Ethylene Glycol)s Linked to 5'–Fluorouracil via a Urethane or Urea Bond", *Drug Des. & Disc.*, 1992, 9, 93–105.

Rao, M.V. et al., "Dibenzoyl Tetrasulphide—A Rapid Sulphur Transfer Agent in the Synthesis of Phosphorothioate Analogues of Oligonucleotides", *Tetrahedron Letts.*, 1992, 33, 4839–4842 (Issue No. 33).

Ravasio, N. et al., "Selective Hydrogenations Promoted by Copper Catalysts. 1. Chemoselectivity, Regioselectivity, and Stereoselectivity in the Hydrogenation of 3–Substituted Steroids", *J. Org. Chem.*, 1991, 56, 4329–4333.

Secrist, J.A. et al., "Synthesis and Biological Activity of 4'–Thionucleosides", 10th International Roundtable: Nucleosides, Nucleotides and their Biological Applications, Sep. 16–20, 1992, Abstract 21, Park City, Utah, 40.

Spiller et al., "The uptake kinetics of chimeric oligodeoxynucleotide analogues in human leukaemia MOLT–4 cells", *Anti–Cancer Drug Design*, 1992, 7, 115–129.

Stec, W.J. et al., "Stereospecific Synthesis of P–chiral Analogs of oligonucleotides", *Methods in Molecular Biology: Protocols for Oligonucleotides and Analogs*, Agrawal, S. (ed.), Humana Press, Totowa, NJ, 1993, Chapter 14, 285–313.

Stec, W.J. et al., "Bis (O,O–Diisopropoxy Phosphinothioyl) Disulfide—A Highly Efficient Sulfurizing Reagent for Cost–Effective Synthesis of Oligo(Nucleoside Phosphorothioate)s", *Tetrahedron Letts.*, 1993, 34, 5317–5320 (Issue No. 33).

Stec, W.J. et al., "Novel route to oligo(deoxyribonucleoside phosphorothioates). Stereocontrolled synthesis of P–chiral oligo(deoxyribonucleoside phosphorothioates)", *Nucl. Acids Res.*, 1991, 19, 5883–5888 (Issue No. 21).

Uhlmann, E. et al., "Antisense Oligonucleotides: A New Therapeutic Principle", *Chem. Reviews*, 1990, 90, 544–584 (Jun. 1990).

Varma, "Synthesis of Oligoncleotide Analogues with Modified Backbones", *Synlett,* 1993, 621–637 (Sep. 1993).

Vu, H. et al, "Internucleotide Phosphite Sulfurization with Tetraethylthiuram Disulfide. Phosphorothioate Oligonucleotide Synthesis via Phosphoramidite Chemistry", *Tetrahedron Letts.,* 1991, 32, 3005–3008 (Issue No. 26).

Wolter, A. et al., Polymer Support Oligonucleotide Synthesis XX: Synthesis of a Henhectacosa Deoxynucleotide by use of a Dimeric Phosphoramidite *Nucleosides & Nucleotides,* 1986, 5, 65–77 (Issue No. 1).

Wright, P. et al., "Large Scale Synthesis of Oligonucleotides via phosphoramidite Nucleosides and a High–loaded Polystyrene Support", *Tetrahedron Letts.,* 1993, 34, 3373–3376 (Issue No. 21).

Wu, H. et al., "Inhibition of in vitro transcription by specific double-stranded oligodeoxyribonucleotides", *Gene,* 1990, 89, 203–209.

Xu, Q. et al., "Use of 1,2,4–dithiazolidine (DtsNH) and 3–ethoxy–1,2,4–dithiazoline–5–one (EDITH) for synthesis of phosphorothioate–containing oligodeoxyribonucleotides", *Nucl. Acids Res.,* 1996, 24, 1602–1607 (Issue No. 9).

Xu, Q. et al., "Efficient introduction of phosphorothioates into RNA oligonucleotides by 3–ethoxy–1,2,4–dithiazoline–5–one (EDITH)", *Nucl. Acids Res.,* 1996, 24, 3643–3644 (Issue No. 18).

PCT International Search Report dated Sep. 17, 1999, 6 pages.

* cited by examiner

PROCESSES FOR THE SYNTHESIS OF OLIGONUCLEOTIDE COMPOUNDS

FIELD OF THE INVENTION

This invention is directed to methods for the preparation of protected forms of oligonucleotides wherein at least one of the phosphate moieties of the oligonucleotide is protected with a protecting group that is removable by intracellular enzymes. The invention is further directed to methods for preparing such oligonucleotides that contain radioactive labels. The invention also is directed to the preparation of amidite reagents for preparing these oligonucleotides. The methods of the invention can be used to prepare prodrug forms of oligonucleotides and chimeric oligonucleotides that are modified with certain functional groups that are cleavable by intercellular enzymes to release the oligonucleotide from its prodrug form. The oligonucleotides prepared by the methods of the invention can be of any known sequence, preferably one that is complementary to a target strand of a mRNA. The compounds produced by the methods of the invention are useful for therapeutics, diagnostics, and as research reagents.

BACKGROUND OF THE INVENTION

Oligonucleotides and their analogs have been developed and used in molecular biology in a variety of procedures as probes, primers, linkers, adapters, and gene fragments. Modifications to oligonucleotides used in these procedures include labeling with nonisotopic labels, e.g. fluorescein, biotin, digoxigenin, alkaline phosphatase, or other reporter molecules. Other modifications have been made to the ribose phosphate backbone to increase the nuclease stability of the resulting analog. Examples of such modifications include incorporation of methyl phosphonate, phosphorothioate, or phosphorodithioate linkages, and 2'-O-methyl ribose sugar units. Further modifications include those made to modulate uptake and cellular distribution. With the success of these compounds for both diagnostic and therapeutic uses, there exists an ongoing demand for improved oligonucleotides and their analogs.

It is well known that most of the bodily states in multicellular organisms, including most disease states, are effected by proteins. Such proteins, either acting directly or through their enzymatic or other functions, contribute in major proportion to many diseases and regulatory functions in animals and man. For disease states, classical therapeutics has generally focused upon interactions with such proteins in efforts to moderate their disease-causing or disease-potentiating functions. In newer therapeutic approaches, modulation of the actual production of such proteins is desired. By interfering with the production of proteins, the maximum therapeutic effect may be obtained with minimal side effects. It is therefore a general object of such therapeutic approaches to interfere with or otherwise modulate gene expression, which would lead to undesired protein formation.

One method for inhibiting specific gene expression is with the use of oligonucleotides, especially oligonucleotides which are complementary to a specific target messenger RNA (mRNA) sequence. Several oligonucleotides are currently undergoing clinical trials for such use. Phosphorothioate oligonucleotides are presently being used as such antisense agents in human clinical trials for various disease states, including use as antiviral agents.

Transcription factors interact with double-stranded DNA during regulation of transcription. Oligonucleotides can serve as competitive inhibitors of transcription factors to modulate their action. Several recent reports describe such interactions (see Bielinska, et. al., *Science* 1990, 250, 997–1000; and Wu, et. al., *Gene* 1990, 89, 203–209).

In addition to such use as both indirect and direct regulators of proteins, oligonucleotides and their analogs also have found use in diagnostic tests. Such diagnostic tests can be performed using biological fluids, tissues, intact cells or isolated cellular components. As with gene expression inhibition, diagnostic applications utilize the ability of oligonucleotides and their analogs to hybridize with a complementary strand of nucleic acid. Hybridization is the sequence specific hydrogen bonding of oligomeric compounds via Watson-Crick and/or Hoogsteen base pairs to RNA or DNA. The bases of such base pairs are said to be complementary to one another.

Oligonucleotides and their analogs are also widely used as research reagents. They are useful for understanding the function of many other biological molecules as well as in the preparation of other biological molecules. For example, the use of oligonucleotides and their analogs as primers in PCR reactions has given rise to an expanding commercial industry. PCR has become a mainstay of commercial and research laboratories, and applications of PCR have multiplied. For example, PCR technology now finds use in the fields of forensics, paleontology, evolutionary studies and genetic counseling. Commercialization has led to the development of kits which assist non-molecular biology-trained personnel in applying PCR. Oligonucleotides and their analogs, both natural and synthetic, are employed as primers in such PCR technology.

Oligonucleotides and their analogs are also used in other laboratory procedures. Several of these uses are described in common laboratory manuals such as *Molecular Cloning, A Laboratory Manual*, Second Ed., J. Sambrook, et al., Eds., Cold Spring Harbor Laboratory Press, 1989; and *Current Protocols In Molecular Biology*, F. M. Ausubel, et al., Eds., Current Publications, 1993. Such uses include as synthetic oligonucleotide probes, in screening expression libraries with antibodies and oligomeric compounds, DNA sequencing, in vitro amplification of DNA by the polymerase chain reaction, and in site-directed mutagenesis of cloned DNA. See Book 2 of *Molecular Cloning, A Laboratory Manual*, supra. See also "DNA-protein interactions and The Polymerase Chain Reaction" in Vol. 2 of *Current Protocols In Molecular Biology*, supra.

Oligonucleotides and their analogs can be synthesized to have customized properties that can be tailored for desired uses. Thus a number of chemical modifications have been introduced into oligomeric compounds to increase their usefulness in diagnostics, as research reagents and as therapeutic entities. Such modifications include those designed to increase binding to a target strand (i.e. increase their melting temperatures, Tm, to assist in identification of the oligonucleotide or an oligonucleotide-target complex, to increase cell penetration, to stabilize against nucleases and other enzymes that degrade or interfere with the structure or activity of the oligonucleotides and their analogs, to provide a mode of disruption (terminating event) once sequence-specifically bound to a target, and to improve the pharmacokinetic properties of the oligonucleotide.

The complementarity of oligonucleotides has been used for inhibition of a number of cellular targets. Such complementary oligonucleotides are commonly described as being antisense oligonucleotides. Various reviews describing the results of these studies have been published including Progress In Antisense Oligonucleotide Therapeutics, Crooke, S. T. and Bennett, C. F., Annu. *Rev. Pharmacol. Toxicol.*, 1996, 36, 107–129. These oligonucleotides have proven to be very powerful research tools and diagnostic agents. Further, certain oligonucleotides that have been shown to be efficacious are currently in human clinical trials.

Antisense therapy involves the use of oligonucleotides having complementary sequences to target RNA or DNA. Upon binding to a target RNA or DNA, an antisense oligonucleotide can selectively inhibit the genetic expression of these nucleic acids or can induce other events such as destruction of a targeted RNA or DNA or activation of gene expression.

Destruction of targeted RNA can be effected by activation of RNase H. RNase H is an endonuclease that cleaves the RNA strand of DNA:RNA duplexes. This enzyme, thought to play a role in DNA replication, has been shown to be capable of cleaving the RNA component of the DNA:RNA duplexes in cell free systems as well as in Xenopus oocytes.

RNase H is very sensitive to structural alterations in antisense oligonucleotides. To activate RNase H, a DNA:RNA structure must be formed. Therefore for an antisense oligonucleotide to activate RNase H, at least a part of the oligonucleotide must be DNA like. To be DNA like requires that the sugars of the nucleotides of the oligonucleotide have a 2'-deoxy structure and the phosphate linkages of the oligonucleotide have negative charges. Chemical modifications of the DNA portion of oligonucleotide at either of these two positions resulted in oligonucleotides that are no longer substrates for RNase H.

However, 2'-deoxy nucleotides have weaker binding affinity to their counterpart ribonucleotides than like ribonucleotides would, i.e., RNA:RNA binding is stronger than DNA:RNA binding, and the presence of the negative charges has been thought to contribute to reduced cellular uptake of the antisense oligonucleotide. Therefore, to circumvent the limitations of DNA like oligonucleotides, chimeric oligonucleotides have been synthesized wherein a DNA like central portion having 2'-deoxy nucleotides and negative charged phosphate linkages is included as the center of a large oligonucleotide that has other types of nucleotides on either side of the DNA like center portion. The center portion must be of a certain size in order to activate RNase H upon binding of the oligonucleotide to a target RNA.

There remains a continuing long-felt need for modified antisense compounds that incorporate chemical modifications for improving characteristics such as compound stability, cellular uptake and detectability, but are also available for regulation of target RNA through each of the known mechanisms of action of antisense compounds. Such regulation of target RNA would be useful for therapeutic purposes both in vivo and ex vivo and, as well as, for diagnostic reagents and as research reagents including reagents for the study of both cellular and in vitro events.

Labeling with radioactive isotopes provides an efficient tool for studying pharmacological properties of antisense oligonucleotides. As with other classes of drug compounds, this novel class of therapeutics requires high sensitivity radiodetection for evaluation of distribution of antisense agents in tissues and assessment of their metabolic fate. Several methods to introduce $^{35}S$ at the internucleosidic thiophosphate of $^3H$ or $^{14}C$ at the base moiety of synthetic oligonucleotides have been reported. Among these labels, $^{14}C$ offers the highest specific activity and the longest half-life. Considering catabolism of nucleic acids, labeling with $^{14}C$ at the C-2 position of thymidine results in formation of $^{14}CO_2$ which is cumbersome to trap and analyze. On the other hand, labeling at either the C-4 or C-6 position leads to β-aminoisobutyric acid as the metabolite which is much more convenient to analyze.

There remains a need for methods of preparing labeled antisense oligonucleotides that overcome the foregoing difficulties. The present invention is directed to the foregoing important ends.

SUMMARY OF THE INVENTION

The present invention is directed to methods for the preparation of oligonucleotides having at least one bioreversible protecting group that confers enhanced chemical and biophysical properties. The bioreversible protecting groups further lend nuclease resistance to the oligonucleotides. The bioreversible protecting groups are removed in a cell, in the cell cytosol, or in vitro in cytosol extract, by endogenous enzymes. In certain preferred oligonucleotides of the invention the bioreversible protecting groups are designed for cleavage by carboxyesterases to yield unprotected oligonucleotides.

In one aspect of the present invention, methods are provided for the preparation of oligomeric compounds having at least one moiety having the Formula I:

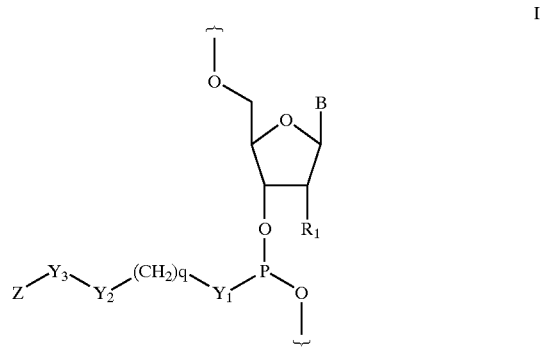

wherein:
Z is aryl having 6 to about 14 carbon atoms or alkyl having from one to about six carbon atoms;
$Y_1$ is O or S;
$Y_2$ is O or S;
$Y_3$ is C(=O) or S;
q is 2 to about 4;
$R_1$ is H, OH, F, or a group of formula $R_7$—$(R_8)_n$;
$R_7$ is $C_3$–$C_{20}$ alkyl, $C_4$–$C_{20}$ alkenyl, $C_2$–$C_{20}$ alkynyl, $C_1$–$C_{20}$ alkoxy, $C_2$–$C_{20}$ alkenyloxy, or $C_2$–$C_{20}$ alkynyloxy;
$R_8$ is hydrogen, amino, protected amino, halogen, hydroxyl, thiol, keto, carboxyl, nitro, nitroso, nitrile, trifluoromethyl, trifluoromethoxy, O-alkyl, S-alkyl, NH-alkyl, N-dialkyl, O-aryl, S-aryl, NH-aryl, O-aralkyl, S-aralkyl, NH-aralkyl, N-phthalimido, imidazole, azido, hydrazino, hydroxylamino, isocyanato, sulfoxide, sulfone, sulfide, disulfide, silyl, aryl, heterocycle, carbocycle, intercalator, reporter molecule, conjugate, polyamine, polyamide, polyalkylene glycol, polyether, a group that enhances the pharmacodynamic properties of oligonucleotides, a group that enhances the pharmacokinetic properties of oligonucleotides, or a group of formula (—O—$X_3$)$_p$, where p is 1 to about 10 and $X_3$ is alkyl having from one to about 10 carbons;

B is a naturally occurring or non-naturally occurring nucleobase that is optionally protected and optionally radiolabeled.

These methods comprise the steps of providing a compound having the Formula II:

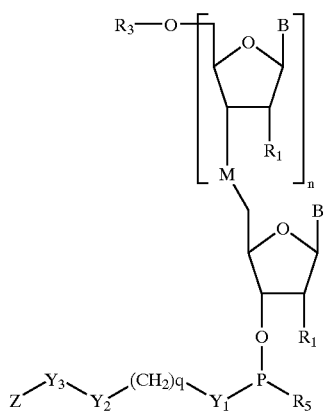

II wherein:
- $R_3$ is hydrogen, a hydroxyl protecting group, or a linker connected to a solid support;
- M is an optionally protected internucleotide linkage;
- each B, independently is a naturally occurring or non-naturally occurring nucleobase that is optionally protected and optionally radiolabeled;
- n is 0 to about 50;
- $R_5$ is —$N(R_6)_2$, or a heterocycloalkyl or heterocycloalkenyl ring containing from 4 to 7 atoms and up to 3 heteroatoms selected from nitrogen, sulfur, and oxygen;
- $R_6$ is straight or branched chain alkyl having from 1 to 10 carbons.

Compounds of Formula II are then reacted with compounds having Formula III:

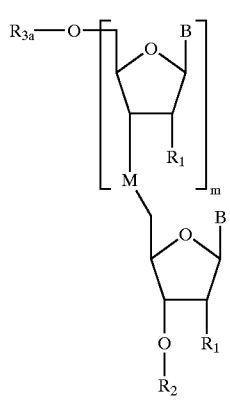

III (wherein $R_{3a}$ is hydrogen; m is 0 to about 50; and $R_2$ is a hydroxyl protecting group, or a linker connected to a solid support, provided that $R_2$ and $R_3$ are not both simultaneously a linker connected to a solid support), thereby forming the oligomeric compound.

In some preferred embodiments, the methods of the invention further comprise oxidizing or sulfurizing the oligomeric compound to form a further compound having Formula III, wherein $R_3$ is hydrogen, a hydroxyl protecting group, or a linker connected to a solid support, and where m is increased by n+1. In further preferred embodiments, the methods of the invention include a capping step, which can be performed prior to or subsequent to oxidation or sulfurization.

In preferred embodiments, the methods of the invention further comprise cleaving the oligomeric compound to produce a compound having the Formula IV:

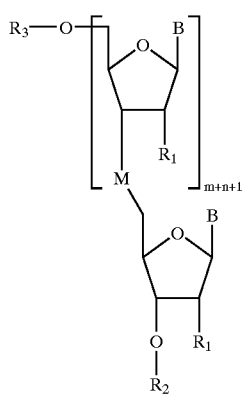

IV

In some particularly preferred embodiments, the cleaving step occurs enzymatically, more preferably in vivo.

In some preferred embodiments, the compound of Formula II is formed by reaction of a compound having Formula V:

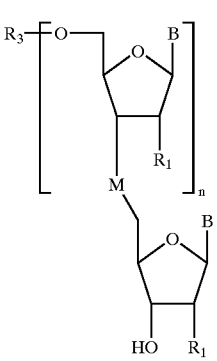

V with a compound having the Formula VI:

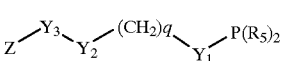

VI in the presence of an acid.

In further preferred embodiments, the compound of Formula II is obtained by reaction of a compound having Formula V with a chlorophosphine compound of formula $ClP[i-Pr_2N]_2$, followed by reaction with a compound of Formula XX:

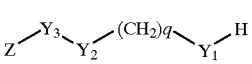

XX in the presence of an acid.

Also provided in accordance with the present invention are methods for the preparation of a phosphoramidite of Formula II:

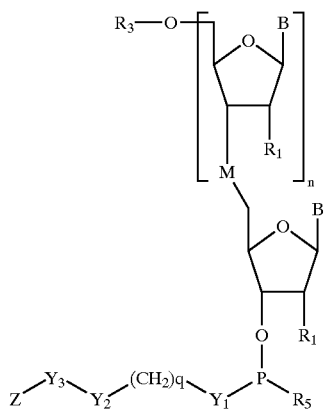

wherein:

$R_3$ is hydrogen, a hydroxyl protecting group, or a linker connected to a solid support;

Z is aryl having 6 to about 14 carbon atoms or alkyl having from one to about six carbon atoms;

$Y_1$ is O or S;

Y2 is O or S;

$Y_3$ is C(=O) or S;

q is 2 to about 4;

M is an optionally protected internucleotide linkage;

each B, independently is a naturally occurring or non-naturally occurring nucleobase that is optionally protected and optionally radiolabeled;

n is 0 to about 50;

$R_1$ is H, OH, F, or a group of formula $R_7$—$(R_8)_n$;

R7 is $C_3$–$C_{20}$ alkyl, $C_4$–$C_{20}$ alkenyl, $C_2$–$C_{20}$ alkynyl, $C_1$–$C_{20}$ alkoxy, $C_2$–$C_{20}$ alkenyloxy, or $C_2$–$C_{20}$ alkynyloxy;

$R_8$ is hydrogen, amino, protected amino, halogen, hydroxyl, thiol, keto, carboxyl, nitro, nitroso, nitrile, trifluoromethyl, trifluoromethoxy, O-alkyl, S-alkyl, NH-alkyl, N-dialkyl, O-aryl, S-aryl, NH-aryl, O-aralkyl, S-aralkyl, NH-aralkyl, N-phthalimido, imidazole, azido, hydrazino, hydroxylamino, isocyanato, sulfoxide, sulfone, sulfide, disulfide, silyl, aryl, heterocycle, carbocycle, intercalator, reporter molecule, conjugate, polyamine, polyamide, polyalkylene glycol, polyether, a group that enhances the pharmacodynamic properties of oligonucleotides, a group that enhances the pharmacokinetic properties of oligonucleotides, or a group of formula (—O—$X_3)_p$, where p is 1 to about 10 and $X_3$ is alkyl having from one to about 10 carbons;

$R_5$ is —$N(R_6)_2$, or a heterocycloalkyl or heterocycloalkenyl ring containing from 4 to 7 atoms and up to 3 heteroatoms selected from nitrogen, sulfur, and oxygen;

$R_6$ is straight or branched chain alkyl having from 1 to 10 carbons.

Such methods comprise the steps of providing a compound Formula V:

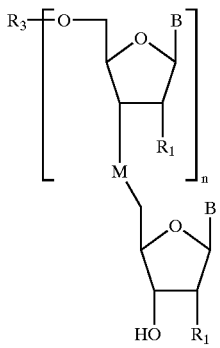

and reacting the compound with a diaminohalophosphine of Formula:

(wherein X is halogen, with chlorine being preferred), thereby producing a phosphordiamidite of Formula:

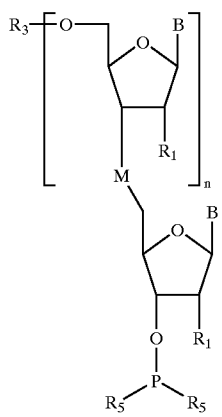

The phosphorordiamidite is then contacted with a regent of Formula XX:

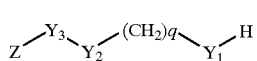

to produce the phosphoramidite.

Also provided in accordance with the present invention are methods for the preparation of a phosphoramidite of Formula II:

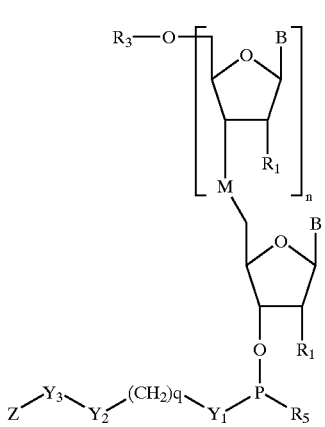

II

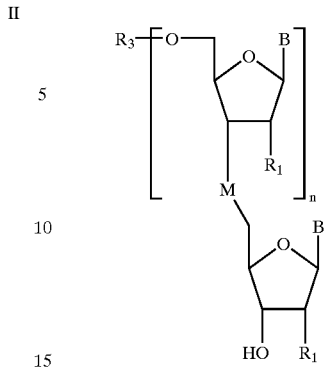

V wherein:

R$_3$ is hydrogen, a hydroxyl protecting group, or a linker connected to a solid support;

z is alkyl having from one to about six carbon atoms;

Y$_1$ is O or S;

Y$_2$ is O or S;

Y$_3$ is O or S;

q is 2 to about 4;

M is an optionally protected internucleotide linkage;

each B, independently is a naturally occurring or non-naturally occurring nucleobase that is optionally protected and optionally radiolabeled;

n is 0 to about 50;

R$_1$ is H, OH, F, or a group of formula R$_7$—(R$_8$)$_n$;

R$_7$ is C$_3$–C$_{20}$ alkyl, C$_4$–C$_{20}$ alkenyl, C$_2$–C$_{20}$ alkynyl, C$_1$–C$_{20}$ alkoxy, C$_2$–C$_{20}$ alkenyloxy, or C$_2$–C$_{20}$ alkynyloxy;

R$_8$ is hydrogen, amino, protected amino, halogen, hydroxyl, thiol, keto, carboxyl, nitro, nitroso, nitrile, trifluoromethyl, trifluoromethoxy, O-alkyl, S-alkyl, NH-alkyl, N-dialkyl, O-aryl, S-aryl, NH-aryl, O-aralkyl, S-aralkyl, NH-aralkyl, N-phthalimido, imidazole, azido, hydrazino, hydroxylamino, isocyanato, sulfoxide, sulfone, sulfide, disulfide, silyl, aryl, heterocycle, carbocycle, intercalator, reporter molecule, conjugate, polyamine, polyamide, polyalkylene glycol, polyether, a group that enhances the pharmacodynamic properties of oligonucleotides, a group that enhances the pharmacokinetic properties of oligonucleotides, or a group of formula (—O—X$_3$)$_p$, where p is 1 to about 10 and X$_3$ is alkyl having from one to about 10 carbons;

R$_5$ is —N(R$_6$)$_2$, or a heterocycloalkyl or heterocycloalkenyl ring containing from 4 to 7 atoms and up to 3 heteroatoms selected from nitrogen, sulfur, and oxygen;

R$_6$ is straight or branched chain alkyl having from 1 to 10 carbons.

These methods comprise the steps of providing a compound Formula V:

and reacting the compound with a compound of Formula:

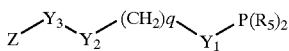

wherein:

Z is alkyl having from one to about six carbon atoms;

Y$_1$ is O or S;

Y$_2$ is O or S;

Y$_3$ is C(=O) or S;

q is 2 to about 4;

R$_5$ is —N(R$_6$)$_2$, or a heterocycloalkyl or heterocycloalkenyl ring containing from 4 to 7 atoms and up to 3 heteroatoms selected from nitrogen, sulfur, and oxygen;

R$_6$ is straight or branched chain alkyl having from 1 to 10 carbons;

thereby producing the phosphordiamidite.

In some preferred embodiments, the compound of Formula:

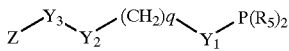

is formed by the reaction of a compound of Formula:

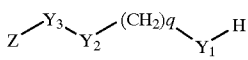

with a compound of Formula:

in the presence of an acid.

In preferred embodiments of the foregoing methods, Z is methyl, t-butyl or phenyl, with t-butyl being preferred. In some particularly preferred embodiments, n is 0.

In some preferred embodiments of the foregoing methods, R$_2$ is a linker to a solid support.

In preferred embodiments of the foregoing methods, Y$_1$ and Y$_2$ are each O and Y$_3$ is C(=O), or Y$_1$ and Y$_2$ are each S and Y$_3$ is C(=O), or Y$_1$ is S and Y$_2$ is O and Y$_3$ is C(=O). In especially preferred embodiments, Y$_1$ is O and Y$_2$ is S and Y3 is C(=O).

In some preferred embodiments of the foregoing methods, each R$_6$ is isopropyl. In some especially preferred embodiments, n is 0; R3 is H, $R_5$ is diisopropylamino; $Y_1$ is O; $Y_2$ is S; Y3 is C(=O); and Z is methyl, phenyl or t-butyl, with t-butyl being preferred.

In some preferred embodiments of the foregoing methods, B radiolabeled nucleobase. In more preferred embodiments, the radiolabeled nucleobase has the formula:

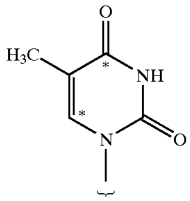

wherein denotes a $^{14}C$ atom.

In preferred embodiments of the foregoing methods, M is an optionally protected phosphite, phosphodiester, phosphotriester, phosphorothioate, phosphorodithioate, or alkyl phosphonate internucleotide linkage. In especially preferred embodiments, M is a phosphite, phosphodiester, phosphotriester, phosphorothioate, phosphorodithioate, or alkyl phosphonate internucleotide linkage protected with protecting group of formula $-Y_1-(CH_2)_q-Y_2-Y_3-Z$.

BRIEF DESCRIPTION OF THE DRAWINGS

The numerous objects and advantages of the present invention may be better understood by those skilled in the art by reference to the accompanying non-scale figures, in which.

DETAILED DESCRIPTION OF THE INVENTION

Figure 1:
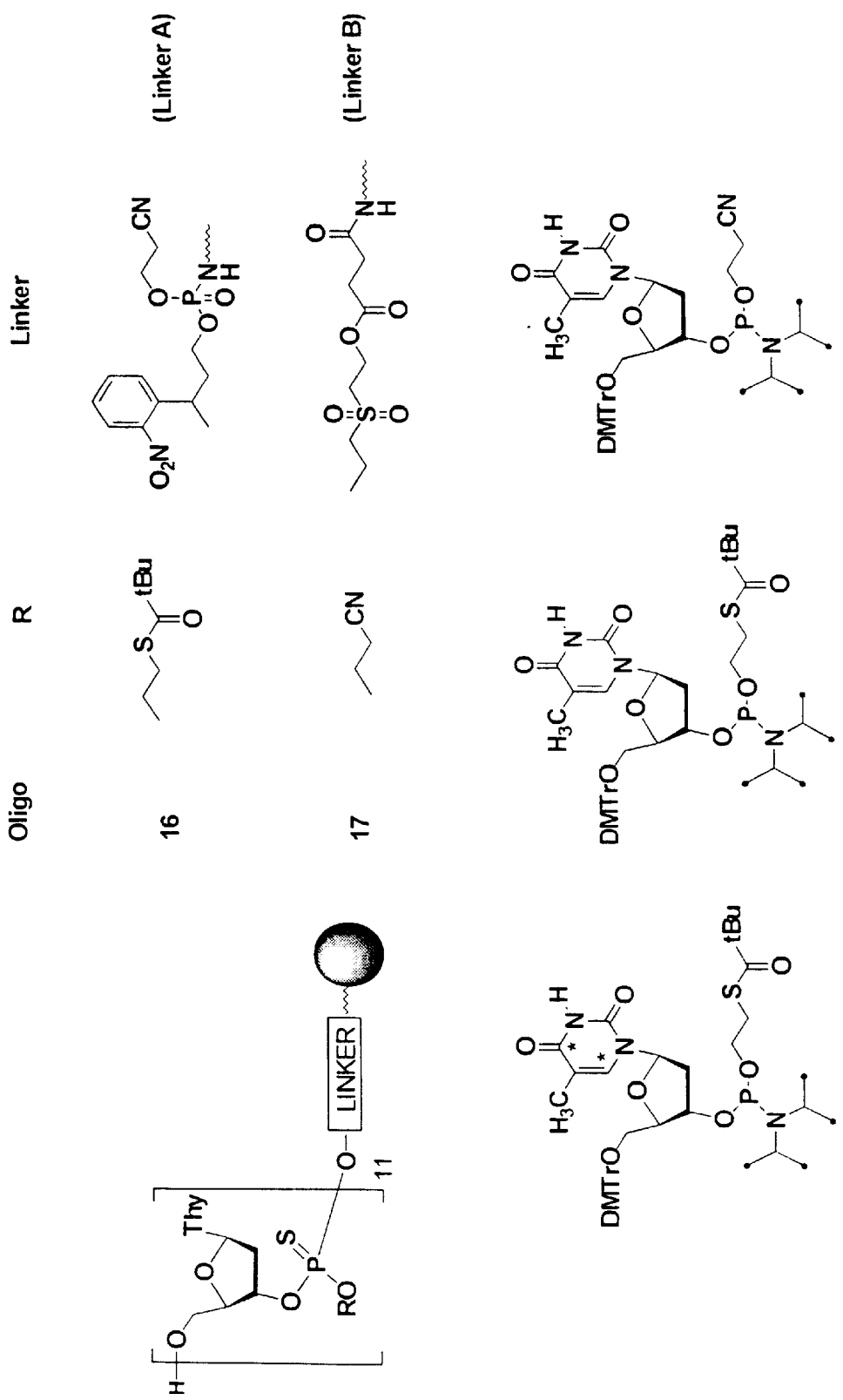
FIG. 1 shows compounds 15–19.

The present invention relates to methods for the preparation of oligonucleotides having at least one bioreversible protecting group. The bioreversible protecting groups contribute to certain enhanced chemical and biophysical properties of the oligonucleotides including resistance to exo- and endonuclease degradation.

Oligonucleotides represent a new class of compounds that specifically inhibit gene expression by Watson-Crick base pair formation with their targets which usually are known mRNA sequences. After binding to the mRNA, down regulation of gene product expression occurs. Crooke, S. T., *Nucleic Acid Therapeutics In Pharmaceutical Manufacturing International*, Sterling, London, 89 (1992). Use of the first synthesized oligonucleotides, i.e., phosphodiester linked oligonucleotides, was limited by the lack nuclease resistance of these compounds. Nuclease resistance has mainly been resolved by the use of modified oligonucleotides. Milligan, et al., *J. Med. Chem.* 1991, 36, 1923; Varma, *Synlett* 1991, 621; Uhlmann, et al., *Chem. Rev.* 1990, 90, 534.

It has been reported that phosphodiester and phosphorothioate oligonucleotides, both which have a polyanionic character, enter the cell by an active process (adsorptive endocytosis and/or fluid phase endocytosis) and this uptake varies with different cell types. It has been reported that the neutral methylphosphonodiester oligonucleotides enter cells by a different mechanism that is also energy dependent. Spiller, et al., *Anti-Cancer Drug Design* 1991, 7, 115. Certain increases in penetration of the oligonucleotides into cell has been achieved by derivatizing oligonucleotides with poly L-lysine, cholesterol or other like moieties or by encapsulation into liposomes.

In one aspect, the present invention is directed to a further approach to assist cellular uptake of oligonucleotides. In this approach a prodrug strategy is utilized wherein a prooligonucleotide is formed that is believed to temporarily mask the negative charges of phosphodiester, phosphorothioate and phosphorodithioate oligonucleotides by the introduction of a bioreversible group on at least some of phosphate groups of these oligomers. The resulting neutral prooligonucleotides have been found to be enzymatically stable against degradative enzymes. While we do not wish to be bound by theory, we believe this will help oligonucleotides to escape from the endosomes should they become embedded therein and will present a completely different bioavailability pattern in relation with their route of administration. A perceived prerequisite of this approach is that bioreversible groups should be selected that have stability in culture medium and that have selective intracellularly hydrolysis after uptake, due to the existence of a greater enzymatic activity in cytosol than in biological fluids.

The present invention is directed to methods for the preparation of oligonucleotides having at least one bioreversible protecting group that have enhanced chemical and biophysical properties for cellular membrane penetration as well as resistance to exo- and endonuclease degradation in vivo. In certain preferred embodiments of the invention, the bioreversible protecting groups are removed in the cell cytosol by endogenous carboxyesterases to yield biologically active oligonucleotide compounds that are capable of hybridizing to and/or having an affinity for specific nucleic acid or peptide sequences thus interacting with endogenous and/or pathogenic biomolecules.

In one aspect of the present invention, methods are provided for the preparation of oligomeric compounds comprising a moiety having at least one moiety of Formula I:

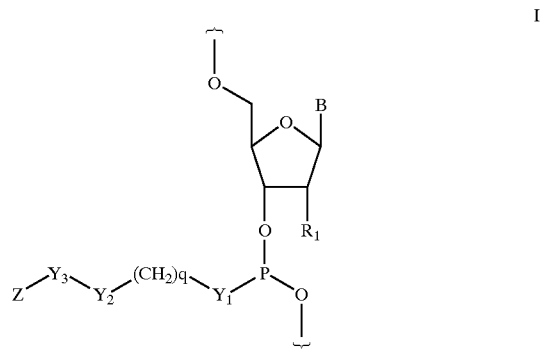

wherein:
Z is aryl having 6 to about 14 carbon atoms or alkyl having from one to about six carbon atoms;
$Y_1$ is O or S;
$Y_2$ is O or S;
$Y_3$ is C(=O) or S;
q is 2 to about 4;
$R_1$ is H, OH, F, or a group of formula $R_7-(R_8)_n$;
$R_7$ is $C_3-C_{20}$ alkyl, $C_4-C_{20}$ alkenyl, $C_2-C_{20}$ alkynyl, $C_1-C_{20}$ alkoxy, $C_2-C_{20}$ alkenyloxy, or $C_2-C_{20}$ alkynyloxy;

$R_8$ is hydrogen, amino, protected amino, halogen, hydroxyl, thiol, keto, carboxyl, nitro, nitroso, nitrile, trifluoromethyl, trifluoromethoxy, O-alkyl, S-alkyl, NH-alkyl, N-dialkyl, O-aryl, S-aryl, NH-aryl, O-aralkyl, S-aralkyl, NH-aralkyl, N-phthalimido, imidazole, azido, hydrazino, hydroxylamino, isocyanato, sulfoxide, sulfone, sulfide, disulfide, silyl, aryl, heterocycle, carbocycle, intercalator, reporter molecule, conjugate, polyamine, polyamide, polyalkylene glycol, polyether, a group that enhances the pharmacodynamic properties of oligonucleotides, a group that enhances the pharmacokinetic properties of oligonucleotides, or a group of formula $(-O-X_3)_p$, where p is 1 to about 10 and $X_3$ is alkyl having from one to about 10 carbons;

B is a naturally occurring or non-naturally occurring nucleobase that is optionally protected and optionally radiolabeled;

comprising the steps of:

providing a compound having the Formula II:

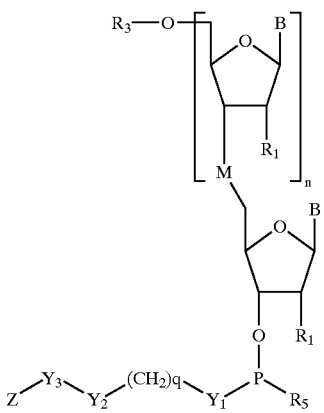

II wherein:

$R_3$ is hydrogen, a hydroxyl protecting group, or a linker connected to a solid support;

M is an optionally protected internucleotide linkage;

each B, independently is a naturally occurring or non-naturally occurring nucleobase that is optionally protected and optionally radiolabeled;

n is 0 to about 50;

$R_5$ is $-N(R_6)_2$, or a heterocycloalkyl or heterocycloalkenyl ring containing from 4 to 7 atoms and up to 3 heteroatoms selected from nitrogen, sulfur, and oxygen;

$R_6$ is straight or branched chain alkyl having from 1 to 10 carbons; and reacting the compound of Formula II with a compound having Formula III:

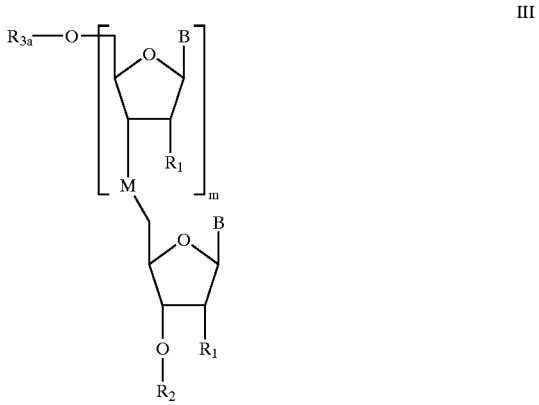

III wherein:

$R_{3a}$ is hydrogen;

m is 0 to about 50;

$R_2$ is a hydroxyl protecting group, or a linker connected to a solid support, provided that $R_2$ and $R_3$ are not both simultaneously a linker connected to a solid support;

to form the oligomeric compound.

The methods of the present invention are useful for the preparation of oligomeric compounds containing monomeric subunits that are joined by a variety of linkages, including phosphite, phosphodiester, phosphotrieter, phosphorothioate, aklyl phosphonate and/or phosphorodithioate linkages. As used herein, the terms "oligomer" and "oligomeric compound" are used to refer to compounds containing a plurality of monomer subunits that are joined by such internucleotide linkages. The term "oligomeric compound" therefore includes naturally occurring oligonucleotides, synthetic oligonucleotides, and their analogs.

In some preferred embodiments of the methods of the invention, a phosphoramidite of Formula II is reacted with a growing nucleotide chain to produce a phosphite compound containing the linkage of Formula I. Preferably, capping, and/or oxidation or sulfurization steps are performed, and the iterative cycle is repeated until the desired nucleobase sequence is attained. This is followed by cleavage to produce a compound of Formula IV.

Methods for coupling compounds of Formula II and Formula III include both solution phase and solid phase chemistries. Representative solution phase techniques are described in U.S. Pat. No. 5,210,264, which is assigned to the assignee of the present invention. In preferred embodiments, the methods of the present invention are employed for use in iterative solid phase oligonucleotide synthetic regimes. Representative solid phase techniques are those typically employed for DNA and RNA synthesis utilizing standard phosphoramidite chemistry, (see, e.g., Protocols For Oligonucleotides And Analogs, Agrawal, S., ed., Humana Press, Totowa, N.J., 1993, hereby incorporated by reference in its entirety). A preferred synthetic solid phase synthesis utilizes phosphoramidites as activated phosphate compounds. In this technique, a phosphoramidite monomer is reacted with a free hydroxyl on the growing oligomer chain to produce an intermediate phosphite compound, which is subsequently oxidized to the $P^V$ state using standard methods. This technique is commonly used for the synthesis of several types of linkages including phosphodiester, phosphorothioate, and phosphorodithioate linkages.

Typically, the first step in such a process is attachment of a first monomer or higher order subunit containing a protected 5'-hydroxyl to a solid support, usually through a linker, using standard methods and procedures known in the art. See for example, *Oligonucleotides And Analogues A Practical Approach*, Ekstein, F. Ed., IRL Press, N.Y, 1991. The support-bound monomer or higher order first synthon is then treated to remove the 5'-protecting group, to form a compound of Formula III wherein $R_2$ is a linker connected to a solid support. Typically, this is accomplished by treatment with acid. The solid support bound monomer is then reacted with a phosphoramidite of Formula II to form a phosphite linkage of Formula I. In some preferred embodiments, synthons of Formula II and Formula III are reacted under anhydrous conditions in the presence of an activating agent such as, for example, 1H-tetrazole, 5-(4-nitrophenyl)-1H-tetrazole, or diisopropylamino tetrazolide.

In preferred embodiments, phosphite or thiophosphite compounds containing a linkage of Formula I are oxidized or sulfurized to produce compounds having a desired internucleotide linkage. The choice of oxidizing or sulfurizing agent will determine whether the linkage of Formula I will be oxidized or sulfurized to, for example, a phosphotriester, thiophosphotriester, or a dithiophosphotriester linkage.

It is generally preferable to perform a capping step either prior to or after oxidation or sulfurization of the phosphite triester, thiophosphite triester, or dithiophosphite triester. As understood by those skilled in the art, the capping step involves attachment of a "cap" moiety to oligonucleotide chains that have not reacted in a given coupling cycle. The cap moiety preferably is reactive with the terminal portion of oligonucleotides that did not participate in the coupling cycle but is not reactive with oligonucleotides that did participate and, moreover, is not itself reactive with the coupling reagents. Such a capping step is generally known to be beneficial by preventing shortened oligomer chains, by blocking chains that have not reacted in the coupling cycle. One representative reagent used for capping is acetic anhydride. Other suitable capping reagents and methodologies can be found in U.S. Pat. No. 4,816,571, issued Mar. 28, 1989, hereby incorporated by reference in its entirety.

Further treatment of the oxidized or sulfurized oligomer with an acid removes the 5'-hydroxyl protecting group, and thus transforms the solid support bound oligomer into a further compound of Formula III wherein $R_{3a}$ is hydrogen. This species is then reacted with a further compound of Formula II to begin the next synthetic iteration. This process is repeated until an oligomer of desired length is produced.

The completed oligomer is then cleaved from the solid support. The cleavage step, which can precede or follow deprotection of protected functional groups, will in preferred embodiments yield a compound having Formula IV wherein $R_2$ is hydrogen. In some preferred embodiments, cleavage of the oligonucleotide from the solid support also removes protecting groups of the internucleotide linkages. Thus, in some preferred embodiments, the linkages between monomeric subunits are converted during cleavage from phosphotriester, thiophosphotriester, or dithiophosphotriester linkages to phosphodiester, phosphorothioate, or phosphorodithioate linkages.

In other preferred embodiments of the invention, cleavage of the oligonucleotide from the solid support does not effect the removal of protecting groups of the internucleotide linkages. In such embodiments, the result of cleavage is a compound of formula IV where $R_2$ is H, and each internucleotide linkage formed by the methods of the invention bear a protecting group of formula $-Y_1-(CH_2)_q-Y_2-Y_3-Z$.

The methods of the present invention are applicable to the synthesis of a wide variety of oligomeric compounds which contain, for example, phosphite, phosphodiester, phosphotriester, phosphorothioate, phosphorodithioate and/or alkylphosphonate internucleotide linkages.

In preferred embodiments, the methods of the invention are used for the preparation of oligonucleotides and their analogs. As used herein, the term "oligonucleotide" is intended to include both naturally occurring and non-naturally occurring (i.e., "synthetic") oligonucleotides. Naturally occurring oligonucleotides are those which occur in nature; for example ribose and deoxyribose phosphodiester oligonucleotides having adenine, guanine, cytosine, thymine and uracil nucleobases. As used herein, non-naturally occurring oligonucleotides are oligonucleotides that contain modified sugar, internucleotide linkage and/or nucleobase moieties. Such oligonucleotide analogs are typically structurally distinguishable from, yet functionally interchangeable with, naturally occurring or synthetic wild type oligonucleotides. Thus, non-naturally occurring oligonucleotides include all such structures which function effectively to mimic the structure and/or function of a desired RNA or DNA strand, for example, by hybridizing to a target.

Representative nucleobases include adenine, guanine, cytosine, uridine, and thymine, as well as other non-naturally occurring and natural nucleobases such as xanthine, hypoxanthine, 2-aminoadenine, 6-methyl and other alkyl derivatives of adenine and guanine, 2-propyl and other alkyl derivatives of adenine and guanine, 5-halo uracil and cytosine, 6-azo uracil, cytosine and thymine, 5-uracil (pseudo uracil), 4-thiouracil, 8-halo, oxa, amino, thiol, thioalkyl, hydroxyl and other 8-substituted adenines and guanines, 5-trifluoromethyl and other 5-substituted uracils and cytosines, 7-methylguanine. Further naturally and non naturally occurring nucleobases include those disclosed in U.S. Pat. No. 3,687,808 (Merigan, et al.), in chapter 15 by Sanghvi, in *Antisense Research and Application*, Ed. S. T. Crooke and B. Lebleu, CRC Press, 1993, in Englisch et al., *Angewandte Chemie*, International Edition, 1991, 30, 613–722 (see especially pages 622 and 623, and in the *Concise Encyclopedia of Polymer Science and Engineering*, J. I. Kroschwitz Ed., John Wiley & Sons, 1990, pages 858–859, Cook, *Anti-Cancer Drug Design* 1991, 6, 585–607). The term "nucleosidic base" is further intended to include heterocyclic compounds that can serve as like nucleosidic bases including certain "universal bases" that are not nucleosidic bases in the most classical sense but serve as nucleosidic bases. Especially mentioned as a universal base is 3-nitropyrrole.

Representative 2' sugar modifications (moiety $R_1$ in the formulas described herein) amenable to the present invention include fluoro, O-alkyl, O-alkylamino, O-alkylalkoxy, protected O-alkylamino, O-alkylaminoalkyl, O-alkyl imidazole, and polyethers of the formula (O-alkyl)$_m$, where m is 1 to about 10. Preferred among these polyethers are linear and cyclic polyethylene glycols (PEGs), and (PEG)-containing groups, such as crown ethers and those which are disclosed by Ouchi, et al., *Drug Design and Discovery* 1992, 9, 93, Ravasio, et al., *J. Org. Chem.* 1991, 56, 4329, and Delgardo et. al., *Critical Reviews in Therapeutic Drug Carrier Systems* 1992, 9, 249. Further sugar modifications are disclosed in Cook, P. D., supra. Fluoro, O-alkyl, O-alkylamino, O-alkyl imidazole, O-alkylaminoalkyl, and alkyl amino substitution is described in U.S. patent application Ser. No. 08/398,901, filed Mar. 6, 1995, entitled Oligomeric Compounds having Pyrimidine Nucleotide(s) with 2' and 5' Substitutions.

Sugars having O-substitutions on the ribosyl ring are also amenable to the present invention. Representative substitutions for ring O include S, $CH_2$, CHF, and $CF_2$, see, e.g., Secrist, et al., Abstract 21, *Program & Abstracts, Tenth International Roundtable, Nucleosides, Nucleotides and their Biological Applications*, Park City, Utah, Sept. 16–20, 1992.

As used herein, the term "alkyl" includes but is not limited to straight chain, branch chain, and alicyclic hydrocarbon groups. Alkyl groups of the present invention may be substituted. Representative alkyl substituents are disclosed in U.S. Pat. No. 5,212,295, at column 12, lines 41–50, hereby incorporated by reference in its entirety.

"Aryl" groups are aromatic cyclic compounds including but not limited to phenyl, naphthyl, anthracyl, phenanthryl, pyrenyl, and xylyl.

In general, the term "hetero" denotes an atom other than carbon, preferably but not exclusively N, O, or S. Accordingly, the term "heterocycloalkyl" denotes an alkyl ring system having one or more heteroatoms (i.e., non-carbon atoms). Preferred heterocycloalkyl groups include, for example, morpholino groups. As used herein, the term "heterocycloalkenyl" denotes a ring system having one or more double bonds, and one or more heteroatoms. Preferred heterocycloalkenyl groups include, for example, pyrrolidino groups.

In some preferred embodiments of the invention $R_2$, $R_3$ or $R_{3a}$ can be a linker connected to a solid support. Solid supports are substrates which are capable of serving as the solid phase in solid phase synthetic methodologies, such as those described in Caruthers U.S. Pat. Nos. 4,415,732; 4,458,066; 4,500,707; 4,668,777; 4,973,679; and 5,132,418; and Koster U.S. Pat. Nos. 4,725,677 and Re. 34,069. Linkers are known in the art as short molecules which serve to connect a solid support to functional groups (e.g., hydroxyl groups) of initial synthon molecules in solid phase synthetic techniques. Suitable linkers are disclosed in, for example, *Oligonucleotides And Analogues A Practical Approach*, Ekstein, F. Ed., IRL Press, N.Y, 1991, Chapter 1, pages 1–23.

Preferred linkers for use in linking the growing oligonucleotide chain to the solid support in some preferred embodiments of the methods of the invention will be cleaved by reagents that do not result in removal of the —$Y_1$—$(CH_2)_q$—$Y_2$—$Y_3$—Z protecting group. One such linker is the oxalyl linker (Alul, R. H., et al., *Nucl. Acids Res.* 1991, 19, 1527) between a LCAA-CPG solid support and the oligomer. Other photolabile supports have been reported (Holmes et al., *J. Org. Chem.* 1997, 62, 2370–2380; Greenberg et al., *Tetrahedron Lett.* 1993, 34, 251–254). The o-nitrobenzyl functionalized solid support has been previously reported (Dell'Aquila et al., *Tetrahedron Lett.* 1997, 38, 5289–5292). Another preferred method of cleavage without removal of internucleoside protecting groups is by irradiation with ultraviolet light in aqueous acetonitrile.

Solid supports according to the invention include those generally known in the art to be suitable for use in solid phase methodologies, including, for example, controlled pore glass (CPG), oxalyl-controlled pore glass (see, e.g., Alul, et al., *Nucleic Acids Research* 1991, 19, 1527, hereby incorporated by reference in its entirety), TentaGel Support, an aminopolyethyleneglycol derivatized support (see, e.g., Wright, et al., *Tetrahedron Letters* 1993, 34, 3373) and Poros, a copolymer of polystyrene/divinylbenzene.

In some preferred embodiments of the invention $R_2$, $R_3$ or $R_{3a}$ can be a hydroxyl protecting group. A wide variety of hydroxyl protecting groups can be employed in the methods of the invention. Preferably, the protecting group is stable under basic conditions but can be removed under acidic conditions. In general, protecting groups render chemical functionalities inert to specific reaction conditions, and can be appended to and removed from such functionalities in a molecule without substantially damaging the remainder of the molecule. Representative hydroxyl protecting groups are disclosed by Beaucage, et al., *Tetrahedron* 1992, 48, 2223–2311, and also in Greene and Wuts, *Protective Groups in Organic Synthesis*, Chapter 2, 2d ed, John Wiley & Sons, New York, 1991. Preferred protecting groups used for $R_2$, $R_3$ and $R_{3a}$ include dimethoxytrityl (DMT), monomethoxytrityl, 9-phenylxanthen-9-yl (Pixyl) and 9-(p-methoxyphenyl)xanthen-9-yl (Mox). The $R_2$ or $R_3$ group can be removed from oligomeric compounds of the invention by techniques well known in the art to form the free hydroxyl. For example, dimethoxytrityl protecting groups can be removed by protic acids such as formic acid, dichloroacetic acid, trichloroacetic acid, p-toluene sulphonic acid or with Lewis acids such as for example zinc bromide. See for example, Greene and Wuts, supra.

In some preferred embodiments of the invention amino groups are appended to alkyl or other groups, such as, for example, 2'-alkoxy groups (e.g., where $R_1$ is alkoxy) Such amino groups are also commonly present in naturally occurring and non-naturally occurring nucleobases. It is generally preferred that these amino groups be in protected form during the synthesis of oligomeric compounds of the invention. Representative amino protecting groups suitable for these purposes are discussed in Greene and Wuts, *Protective Groups in Organic Synthesis*, Chapter 7, 2d ed, John Wiley & Sons, New York, 1991. Generally, as used herein, the term "protected" when used in connection with a molecular moiety such as "nucleobase" indicates that the molecular moiety contains one or more functionalities protected by protecting groups.

Sulfurizing agents used during oxidation to form phosphorothioate and phosphorodithioate linkages include Beaucage reagent (see e.g. Iyer, et.al., *J. Chem. Soc.* 1990, 112, 1253–1254, and Iyer, et.al., *J. Org. Chem.* 1990, 55, 4693–4699); tetraethylthiuram disulfide (see e.g., Vu, et al., *Tetrahedron Lett.* 1991, 32, 3005–3008); dibenzoyl tetrasulfide (see e.g., Rao, et.al., *Tetrahedron Lett.* 1992, 33, 4839–4842); di(phenylacetyl)disulfide (see e.g., Kamer, *Tetrahedron Lett.* 1989, 30, 6757–6760); Bis(O,O-diisopropoxy phosphinothioyl)disulfide (see Stec et al., *Tetrahedron Lett.* 1993, 34, 5317–5320); 3-ethoxy-1,2,4-dithiazoline-5-one (see *Nucleic Acids Research*, 1996 24, 1602–1607, and *Nucleic Acids Research*, 1996 24, 3643–3644); Bis(p-chlorobenzenesulfonyl)disulfide (see *Nucleic Acids Research*, 1995 23, 4029–4033); sulfur, sulfur in combination with ligands like triaryl, trialkyl, triaralkyl, or trialkaryl phosphines.

Useful oxidizing agents used to form the phosphodiester or phosphorothioate linkages include iodine/tetrahydrofuran/water/pyridine or hydrogen peroxide/water or tert-butyl hydroperoxide or any peracid like m-chloroperbenzoic acid. In the case of sulfurization the reaction is performed under anhydrous conditions with the exclusion of air, in particular oxygen whereas in the case of oxidation the reaction can be performed under aqueous conditions.

Oligonucleotides or oligonucleotide analogs according to the present invention hybridizable to a specific target preferably comprise from about 5 to about 50 monomer subunits. It is more preferred that such compounds comprise from about 10 to about 30 monomer subunits, with 15 to 25 monomer subunits being particularly preferred. When used as "building blocks" in assembling larger oligomeric compounds (i.e., as synthons of Formula II), smaller oligomeric compounds are preferred. Libraries of dimeric, trimeric, or higher order compounds of general Formula II can be prepared for use as synthons in the methods of the invention. The use of small sequences synthesized via solution phase chemistries in automated synthesis of larger oligonucleotides enhances the coupling efficiency and the purity of the final oligonucloetides. See for example: Miura, et al., *Chem. Pharm. Bull.* 1987, 35, 833–836; Kumar, et al., *J. Org. Chem.* 1984, 49, 4905–4912; Bannwarth, *Helvetica Chimica Acta* 1985, 68, 1907–1913; Wolter, et al., *Nucleosides and Nucleotides* 1986, 5, 65–77.

The oligonucleotides produced by preferred embodiments of the methods of the invention having bioreversible protecting groups are also referred to in this specification as pro-oligonucleotides. Such pro-oligonucleotides are capable of improved cellular lipid bilayers penetrating potential as well as resistance to exo- and endonuclease degradation in vivo. In cells, the bioreversible protecting groups are removed in the cell cytosol by endogenous carboxyesterases to yield biologically active oligonucleotide compounds that are capable of hybridizing to and/or having an affinity for specific nucleic acid.

The compounds produced by the methods of the invention mitigate one potential problem with the therapeutic use of oligonucleotides of natural composition, i.e., phosphodiester oligonucleotides specifically 1) their very short biological half-lives due to degradation by nucleases which tend to be ubiquitous, and 2) their inherent negative charge and hydrophilic nature which makes it very difficult biophysically for oligonucleotides to pass through lipid cellular membranes.

The methods of the invention can be used to prepare antisense pro-oligonucleotides to synthetic DNA or RNA or mixed molecules of complementary sequences to a target sequence belonging to a gene or to an RNA messenger whose expression they are specifically designed to block or down-regulate. The methods of the invention can be used to prepare antisense oligonucleotides that can be directed against a target messenger RNA sequence or, alternatively against a target DNA sequence, and hybridize to the nucleic acid to which they are complementary. Accordingly, the compounds produced by the methods of the invention effectively block or down-regulate gene expression.

The pro-oligonucleotides produced according to the methods of the invention can also be directed against certain bicatenary DNA regions (homopurine/homopyrimidine sequences or sequences rich in purines/pyrimidines) and thus form triple helices. The formation of a triple helix, at a particular sequence, can block the interaction of protein factors which regulate or otherwise control gene expression and/or may facilitate irreversible damage to be introduced to a specific nucleic acid site if the resulting oligonucleotide is made to possess a reactive functional group.

As used herein, a target nucleic acid shall mean any nucleic acid that can hybridize with a complementary nucleic acid like compound. Further in the context of this invention, "hybridization" shall mean hydrogen bonding, which may be Watson-Crick, Hoogsteen or reversed Hoogsteen hydrogen bonding, between complementary nucleobases. "Complementary" as used herein, refers to the capacity for precise pairing between two nucleobases. For example, adenine and thymine are complementary nucleobases which pair through the formation of hydrogen bonds. "Complementary" and "specifically hybridizable," as used herein, refer to precise pairing or sequence complementarity between a first and a second nucleic acid-like oligomers containing nucleoside subunits. For example, if a nucleobase at a certain position of the first nucleic acid is capable of hydrogen bonding with a nucleobase at the same position of the second nucleic acid, then the first nucleic acid and the second nucleic acid are considered to be complementary to each other at that position. The first and second nucleic acids are complementary to each other when a sufficient number of corresponding positions in each molecule are occupied by nucleobases which can hydrogen bond with each other. Thus, "specifically hybridizable" and "complementary" are terms which are used to indicate a sufficient degree of complementarity such that stable and specific binding occurs between a compound of the invention and a target RNA molecule. It is understood that an oligomeric compound of the invention need not be 100% complementary to its target RNA sequence to be specifically hybridizable. An oligomeric compound is specifically hybridizable when binding of the oligomeric compound to the target RNA molecule interferes with the normal function of the target RNA to cause a loss of utility, and there is a sufficient degree of complementarity to avoid non-specific binding of the oligomeric compound to non-target sequences under conditions in which specific binding is desired, i.e. under physiological conditions in the case of in vivo assays or therapeutic treatment, or in the case of in vitro assays, under conditions in which the assays are performed.

In some preferred embodiments of the methods of the invention, compounds of Formula II are prepared by reaction of a protected nucleoside having Formula V:

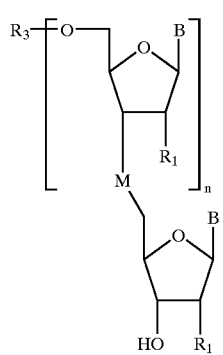

V with a compound having the Formula VI:

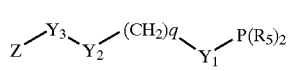

VI in the presence of an acid. Suitable acids include those known in the art to be useful for coupling of phosphoramidites, including, for example, diisopropylammonium tetrazolide.

Compounds of Formula VI are preferably prepared by reacting a compound of formula HO—$Y_1$—$(CH_2)_q$—$Y_2$—$Y_3$—Z with a compound of formula X—$P(R_5)_2$, preferably where $R_5$ is diisopropylamino, and X is halogen, preferably chlorine.

Thus, the present invention also provides methods for the preparation of nucleotide phosphoramidites of Formula II comprising providing a compound of formula:

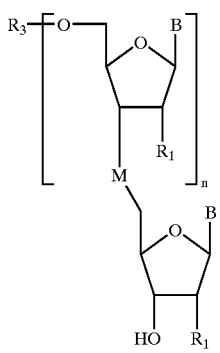

and reacting the compound with a compound of Formula VI:

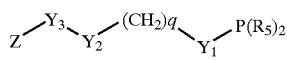

VI to produce the phosphordiamidite.

In further preferred embodiments, methods are provided for the preparation of nucleotide phosphoramidites of Formula II comprising providing a compound Formula:

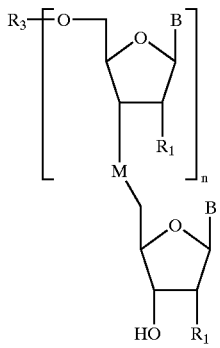

and reacting the compound with a diaminohalophosphine of Formula:

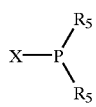

wherein X is halogen, preferably chlorine, to produce a phosphordiamidite of Formula:

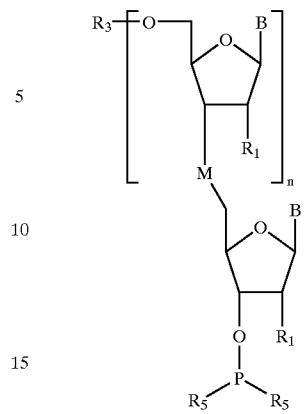

and contacting the nucleoside phosphordiamidite with a reagent of Formula XX:

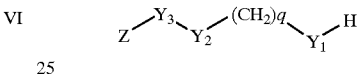

XX to produce the phosphoramidite.

As used herein, the term "contacting" means the placement together of moieties, directly or indirectly, such that they become physically associated with each other. Thus, "contacting" includes, inter alia, placement together in a container.

In some preferred embodiments, the foregoing methods can be performed in a single vessel; i.e., in a "one pot" system, without isolation of the intermediate phosphordiamidite.

Preferably, the diaminohalophosphine of Formula X—P($R_5$)$_2$ is prepared by reaction of $PX_3$, where X is preferably chlorine, with at least two equivalents of an amine having the formula $(R_6)_2N$, in which each of the $R_6$ groups can be the same or different, and are preferably alkyl having 1 to about 10 carbon atoms, more preferably 1 to 6 carbon atoms, with 3 carbon atoms, with isopropyl groups, being especially preferred.

In the compounds and methods of the present invention, M can be a choral phosphorus linkage, for example a phosphorothioate. See Stec, et al., in *Methods in Molecular Biology Vol. 20: Protocols for Oligonucleotides and Analogs*, S. Agrawal, Ed., Humana Press, Totowa, N.J. (1993), at Chapter 14. See also Stec, W. J. et al., *Nucleic Acids Research*, Vol. 19, No. 21, 5883–5888 (1991); and European Patent Application EP 0 506 242 A1.

The oligomeric products of the methods of the invention can be used in diagnostics, therapeutics and as research reagents and kits. They can be used in pharmaceutical compositions by including a suitable pharmaceutically acceptable diluent or carrier. They further can be used for treating organisms having a disease characterized by the undesired production of a protein. The organism should be contacted with an oligonucleotide having a sequence that is capable of specifically hybridizing with a strand of nucleic acid coding for the undesirable protein. Treatments of this type can be practiced on a variety of organisms ranging from unicellular prokaryotic and eukaryotic organisms to multicellular eukaryotic organisms. Any organism that utilizes DNA-RNA transcription or RNA-protein translation as a fundamental part of its hereditary, metabolic or cellular control is susceptible to therapeutic and/or prophylactic treatment in accordance with the invention. Seemingly diverse organisms such as bacteria, yeast, protozoa, algae, all plants and all higher animal forms, including warm-blooded animals, can be treated. Further, each cell of multicellular eukaryotes can be treated, as they include both DNA-RNA transcription and RNA-protein translation as integral parts of their cellular activity. Furthermore, many of the organelles (e.g., mitochondria and chloroplasts) of eukaryotic cells also include transcription and translation mechanisms. Thus, single cells, cellular populations or organelles can also be included within the definition of organisms that can be treated with therapeutic or diagnostic oligonucleotides.

The present invention also provides novel methods for $^{14}C$ labeling of synthetic oligonucleotides. In some preferred embodiments, the methods of the invention include methods for the preparation of mono- or polynucleotide phosphoramidites having Formula I above wherein the nucleobase is radiolabeled, and is preferably [4,6-di-$^{14}C$] thymidine. Thus, in some preferred embodiments, the radiolabeled nucleobase has the formula:

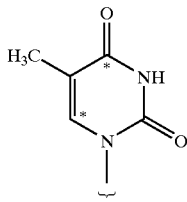

wherein * denotes a $^{14}C$ atom.

The radiolabeled nucleotide phosphoramidites prepared by the methods of the invention can be used in the preparation of labeled oligonucleotides according to the methods of the invention, or according to standard oligonucleotide synthetic regimes. S-Acylthioethyl ("SATE") 4,6-di-$^{14}C$ thymidine phosphoramidite can also be used for the synthesis of normal oligonucleotides. For example this amidite has been used to synthesize $T_{12}$ oligomer phosphorothioate having the $^{14}C$ labels at the 5' end (see Example 24 below).

As will be recognized, the steps of the methods of the present invention need not be performed any particular number of times or in any particular sequence. Additional objects, advantages, and novel features of this invention will become apparent to those skilled in the art upon examination of the following examples thereof, which are intended to be illustrative and not intended to be limiting.

EXAMPLES

General Procedures

All reagents and solvents were purchased from Aldrich Chemical Co. Flash chromatography was performed on silica gel (Baker 40 μm). Thin layer chromatography was performed on Kieselgel 60 F-254 glass plates from E. Merck and compounds were visualized with UV light and sulfuric acid-methanol spray followed by charring. Solvent systems used for thin-layer chromatography and flash chromatography were: A; ethyl acetate-hexanes 1:1. B; ethyl acetate-hexanes-TEA 2:3:0.5. $^1H$ and $^{31}P$ spectra were recorded using a Gemini 200 Varian spectrometer. All reactions were performed under an argon atmosphere and solutions rotary evaporated at 35–45° C. in vacuo using a vacuum pump-vacuum controller combination.

Example 1

2'-Methoxyethyl-5'-O-(4,4'-dimethoxytrityl)-5-methyluridine (S-pivaloyl-2-thioethyl) bis[N,N-Diisopropylphosphoramidite] (2)

To a stirring and cooled solution of 2-methoxyethyl-5'-O-(4,4'-dimethoxytrityl)-5-methyluridine (1) (10 g, 16 mmoles) and diisopropylethylamine (2.7 g, 21 mmoles) in dry dichloromethane (200 ml) in an ice bath was added dropwise a solution of N,N-(diisopropylamino)chlorophosphine (5.2 g, 19 mmoles) in dry dichloromethane. The resulting mixture was stirred at room temperature for 55 minutes. Tetrazole was added (0.6 g, 8.0 mmoles) and a solution of S-(2-hydroxyethyl)thiopivaloate (3.4 g, 21 mmoles) in dry dichloromethane was added dropwise in a periods of 15 minutes. The reaction mixture was stirred for 20 hours at room temperature. At the end of this time, the mixture was diluted with dry $CH_2Cl_2$ (100 ml) and washed with NaHCO3 (80 ml) and brine 3 times (100 ml) each, dried over $MgSO_4$ and evaporated to a solid yellow foam. Flash chromatography using 1:1 (Hexanes:EtOAc) and containing 0.5% triethylamine yielded 10.3 g (70%) of 2. TLC (Hexanes:EtOAc 1:1) $R_f$=0.35. $^{31}P$-NMR ($CD_3CN$): 150.31, 150.54

Example 2

2'-Methoxyethyl-5'-O-(4,4'-dimethoxytrityl)-5-methyluridine (s-acetate-2-thioethyl) bis[N,N-Diisopropylphosphoramidite] (3)

A solution of (1) (10 g, 16mmoles) and diisopropylethylamine (2.7 g, 2 mmoles) in dry dichloromethane (200 ml) was cooled in an ice bath and stirred for 15 minutes. A solution of N,N-(diisopropylamino)chlorophosphine (5.2 g, 19 mmoles) in dry $CH_2Cl_2$ was added dropwise. The resulting mixture was stirred at room temperature for 45 minutes. Tetrazole was added (0.6 g, 8.0 mmoles) and a solution of freshly prepared S-(2-hydroxyethyl)-thioacetate (2.6 g, 21 mmoles) in dry $CH_2Cl_2$ was added in a period of 10 minutes. The reaction mixture was further stirred for 18 hours at room temperature. At the end of this time, the mixture was diluted with dry $CH_2Cl_2$ (100 ml) and washed with $NaHCO_3$ (60 ml) and brine 3 times (80 ml) each and dried over $MgSO_4$ and evaporated to a solid light yellow foam. Purification by flash chromatography using 1:1 (Hexanes:EtOAc) and containing 0.5% triethylamine yielded 8.4 g (60%) of (3). TLC (Hexanes:EtOAc 1:1) $R_f$=0.27, $^{31}P$-NMR ($CD_3CN$) 150.47, 150.63.

Example 3

6-Benzoylamino-2'-deoxy-5'-O-dimethoxytrityl-adenosine-(S-pivaloyl-2-thioethyl) bis[N,N-Diisopropylphosphoramidite] (5)

To a cooled solution of 6-benzoylamino-2'-deoxy-5'-O-dimethyltrityl-adenosine (4) (5 g, 7.3 mmoles) and diisopropylamine (1.22 g, 9.5 mmoles) in dry dichloromethane (100 ml) stirred in an ice bath, was added a solution of N,N-(diisopropylamino)chlorophosphine (2.33 g, 8.76 mmoles) dropwise in dry $CH_2Cl_2$. The resulting mixture was stirred at room temperature for 45 minutes. A solution of S-(2-hydroxyethyl) thiopivaloate (1.42 g, 8.76 mmoles) and tetrazole (0.255 g, 3.65 mmoles) in dry $CH_2Cl_2$ was added in a period of 10 minutes. The reaction mixture was stirred for 22 hours at room temperature. The mixture was diluted with $CH_2Cl_2$ (50 ml) and washed with $NaHCO_3$ (15 ml) and brine (25 ml) dried over $MgSO_4$, filtered and evaporated the solvent to a light yellow foam. Purification by flash chromatography using Hexanes:EtOAc (1:3) and containing 0.5% triethyamine, yielded 5.2 g (70%) of 5. TLC (Hexanes:EtOAc 1:1) $R_f$ .31. $^{31}$P-NMR ($CD_3CN$): 148.97, 149.13.

Example 4

6-Benzoylamino-2'-deoxy-5'-O-dimethyltrityl-cytidine-(S-pivaloyl-2-thioethyl) bis[N,N-Diisopropylphosphoramidite] (7)

The title compound was prepared according to the phosphitylation procedure used in the synthesis of 5. Yield of 7 was 70%. $^{31}$P-NMR ($CD_3CN$): 148.95, 149.25.

Example 5

6-Benzoylamino-2'-deoxy-5'-O-dimethyltrityl-cytidine-(S-benzoyl-2-thioethyl) bis[N,N-Diisopropylphosphoramidite)] (8)

The title compound was prepared according to the phosphitylation procedure used in the synthesis of 5. Yield of 8 was 60. $^{31}$P-NMR ($CD_3CN$): 148.94, 149.40.

Example 6

2-Isobutyryl-2'-deoxy-5'-O-dimethyltrityl-guanosine-(s-pivaloyl-2-thioethyl) bis[N,N-Diisopropylphosphoramidite] (10)

The title compound was prepared according to the phosphitylation procedure used in the synthesis of 5. The purity of 10 was 306 by $^{31}$P-NMR.

Example 7

6-Benzoylamino-2'-deoxy-5'-O-dimethoxytrityl-adenosine-(S-acetate-2-thioethyl) bis[N,N-Diisopropylphosphoramidite] (11)

The title compound was prepared according to the phosphitylation procedure used in the synthesis of 5.

Example 8

6-Benzoylamino-2'-deoxy-5'-O-dimethoxytrityl-cytidine-(S-acetate-2-thioethyl) bis[N,N-Diisopropylphosphoramidite] (12)

The title compound was prepared according to the phosphitylation procedure used in the synthesis of 5.

Example 9

Radiolabeling Of Synthetic Oligonucleotides With The Aid of (S-Pivaloyl 2-Mercaptoethyl) [4,6-Di-$^{14}$c]-3'-O-[(5'-O-(4,4'-Dimethoxytrityl)Thymidyl] N,N-Diisopropylphosphoramidite (S-Pivaloyl 2-mercaptoethyl) [4,6-di-$^{14}$C]-3'-O-[(5'-O-(4,4,-dimethoxytrityl)thymidyl] N,N-Diisopropylphosphoramidite (15)

Bis(N,N-Diisopropylamino)phosphorochloridite (267 mg, 1 mmol) in $CH_2Cl_2$ (2.5 mL)) was added to a magnetically stirred solution of S-pivaloyl 2-mercaptoethanol (162 mg, 1 mmol) and ethyldiisopropylamine (142 mg, 1.1 mmol) in $CH_2Cl_2$ (1 mL for 5 minutes) at −300° C. The mixture was allowed to warm to room temperature and was stirred for 30 minutes to give 13. The volume of solution was adjusted to 4.0 mL, an aliquot (320 µL) was taken and added to dry [4,6-di-$^{14}$C]-5'-O-(4,4'-dimethoxytrityl)thymidine 14 (21.7 mg, 40 (mol; specific activity 25 Ci mol$^{-1}$). Anhydrous 1H-tetrazole (0.45 M in MeCN; 71 (L, 32 (mol) was added, and the mixture was stirred for 40 minutes at room temperature. The reaction was quenched with aqueous $NaHCO_3$ (5%; 2 mL), diluted with saturated NaCl (5 mL) and extracted with benzene (3×10 mL). The extracts were dried over $Na_2SO_4$ and evaporated in vacuo. The residue was dissolved in 50% aqueous MeCN and purified by reversed phase HPLC on a DeltaPak 15 µm C18 300 column (7.8× 300 mm). Isocratic elution with 50% aqueous MeCN for 10 min and with 75% aqueous MeCN for 25 minutes at a flow rate 5 mL min$^{-1}$ was applied. Fractions containing pure 15 ($t_R$=25.5 min) were collected, diluted with water (50 mL) and extracted with benzene (5×10 mL). Extracts were dried over $Na_2SO_4$ and evaporated in vacuo to give S-pivaloyl 2-mercaptoethyl [4,6-di-$^{14}$C]-3'-[(5'-O-(4,4'-dimethoxytrityl)thymidyl] N,N-Diisopropyl-phosphoramidite 15 (20.0 µmol, 50.0%; specific activity 21 Ci mol$^{-1}$).

Example 10

Preparation of $^{14}$C-radiolabeled Oligonucleotides with the Aid of [4,6-di-$^{14}$C]thymidine Building Block (15)

A. Oligonucleotide Synthesis.

Figure 2:
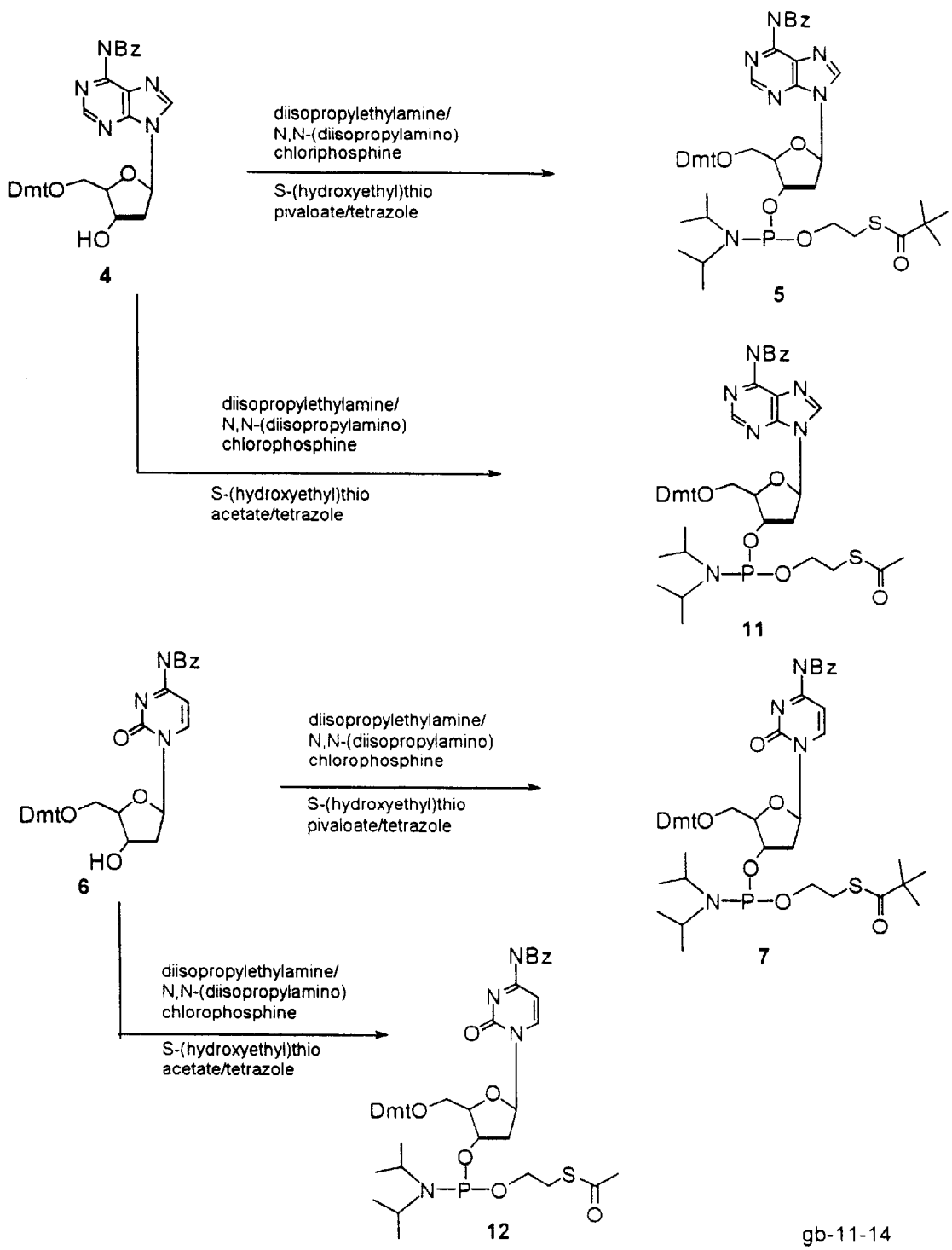
FIG. 2 is a synthetic scheme for compounds 5, 7, 11, and 12.

Non-radioactive 2-(pivaloylthio)ethyl- and 2-cyanoethyl-protected undecathymidylates 16 and 17 were assembled on an ABI 380B DNA Synthesizer using either 2-cyanoethyl 3-(4,4'-dimethoxytrityloxy)-3-(2-nitrophenyl)ethyl phosphate or [[2-(4,4'-dimethoxytrityloxy)ethyl]sulfonyl]ethyl succinyl derivatized CPG (linkers A and B, correspondingly, FIG. 1, phosphoramidite chemistry, and 3H-1,2-benzodithiol-3-one 1,1-dioxide (0.05 M in MeCN) as a sulfur-transfer reagent. For preparation of 16, 5'-O-(4,4'-dimethoxytrityl)thymidyl 2-(pivaloylthio)ethyl N,N-Diisopropylaminophosphite, 18, (FIG. 2) was employed as a building block. Otherwise, commercial thymidine CE phosphoramidite, 19, was used.

B. Radioactive Labeling.

Figure 3:
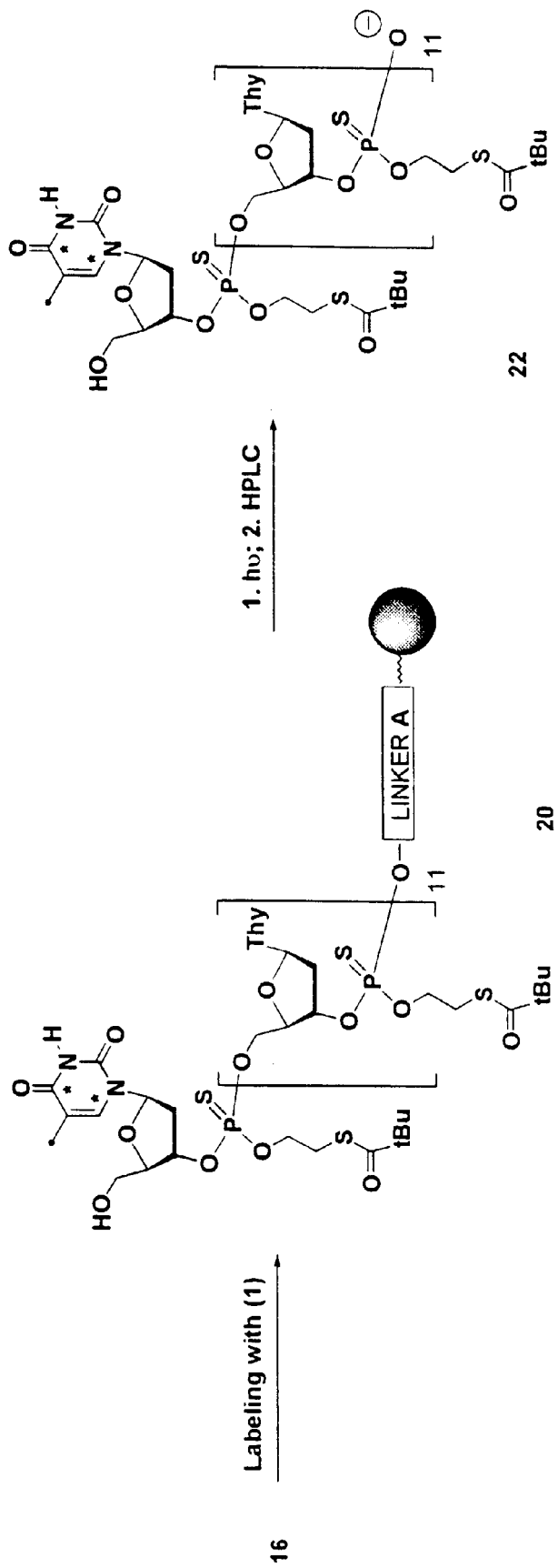
FIG. 3 is a synthetic scheme compound 22.
Figure 4:
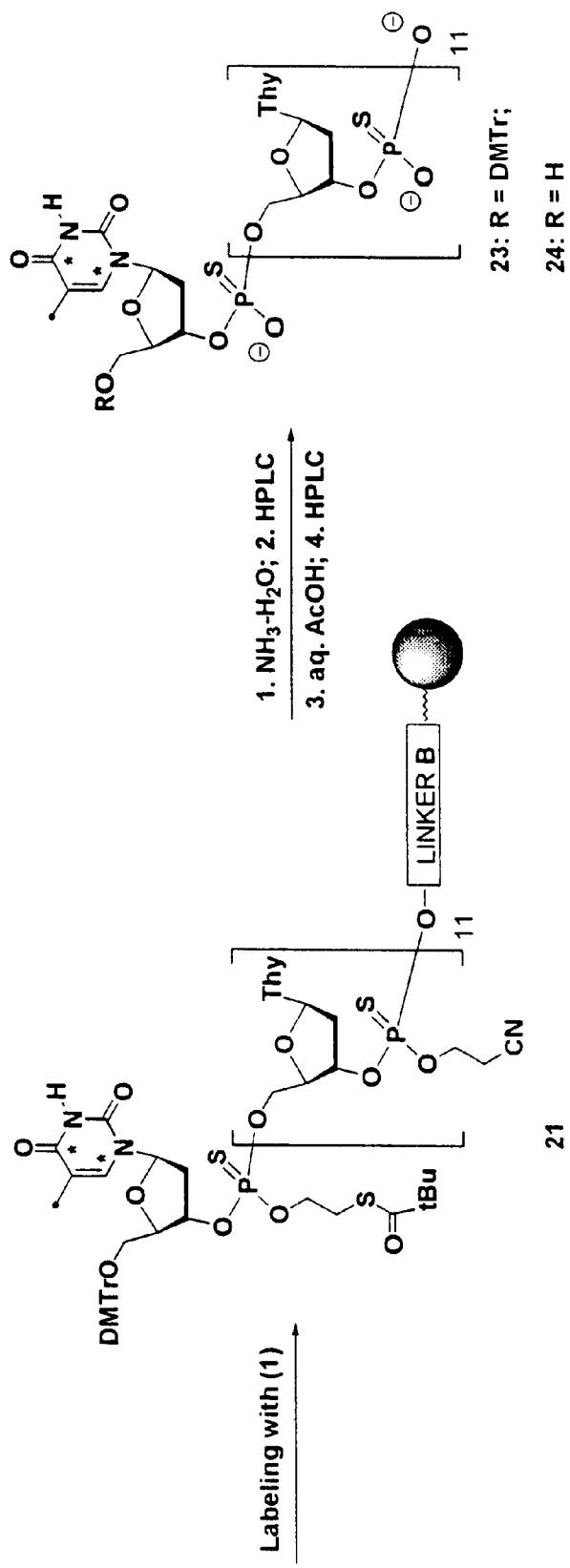
FIG. 4 is a synthetic scheme compounds 23 and 24.

The solid support-bound oligonucleotide 16 or 17 from preceding step was placed into a 5 mL reaction funnel and dried on an oil pump for 2 hours. To this, phosphoramidite 18 (8.9 mg, 10.7 (mol) in MeCN (54 (L) followed by 1H-tetrazole (22 mg, 315 (mol) in MeCN (700 (L) was added, and the mixture was shaken for 3 minutes. The liquid phase was filtered off, and phosphoramidite 15 (13.9 mg, 16.5 µmol, 1000 (Ci) in MeCN (100 µL) and 1H-tetrazole (5.0 mg) in MeCN (160 µL) were added. The coupling mixture was shaken for 15 minutes, the solution was filtered off, and 3H-1,2-benzodithiol-3-one 1,1-dioxide (0.05 M in MeCN; 4 mL) was added. After gentle shaking for 5 minutes, the solution was filtered off, and the solid support was washed with MeCN (5×5 mL) and briefly dried on an oil pump. The solid support was treated with 18 (117 mg) in MeCN (700 µL) and 1H-tetrazole (22 mg) in MeCN (700 (L) for 10 minutes, filtered, treated with 3H-1,2-benzodithiol-3-one 1,1-dioxide (0.05 M in MeCN; 4 mL) for 5 min, and extensively washed with MeCN. The product obtained by labeling 16 was detritylated by treatment with dichloroacetic acid in $CH_2Cl_2$ (3%, 15 mL), washed with MeCN (5×5 mL)

and dried on an oil pump to give support-bound oligonucleotide 20 (FIG. 3). Oligonucleotide 21 prepared by labeling 17 (FIG. 4) was dried on an oil pump and used in 5'-DMT-protected form.

C. Releasing and Isolation of Oligonucleotide 22.

The solid support bound 20 (FIG. 3) was placed in Pyrex test tubes (ca. 50 mg in each tube) and each portion was suspended in 80% aqueous MeCN (3 mL). The suspension was degassed, placed in photochemical reactor, and irradiated for 30 minutes at room temperature. The tube was centrifuged, and supernatant was collected. A fresh portion of 80% aqueous MeCN was added. This procedure was repeated for 5 times until less than 4 OD of oligonucleotide material was released after irradiation for 30 minutes. The collected supernatants were diluted with water to get a solution in 30% aqueous MeCN and filtered. Filtrates were applied on an HPLC column (DeltaPak 15 μ C18 300 Å, 3.9(300 mm; 60% aq. MeCN as buffer A, MeCN as buffer B), and eluted in a linear gradient from 10 to 100% B (30 minutes at a flow rate 5.0 mL min$^{-1}$). The main peak was collected and evaporated in vacuo to afford 22 (659 OD, 32 mg, 100 (μCi). MALDI/TOF MS: found 5592.3; calculated for $C_{204}H_{302}N_{24}O_{85}P_{12}S_{24}$ 5592.0.

An aliquot of 22 (5 OD) was treated with concentrated aqueous ammonia (2 mL) for 8 hours at room temperature, evaporated to dryness, and re-dissolved in water (200 μL) Analysis by ion-exchange chromatography (Resource™ Q—1 mL column (Pharmacia); 0.02 M aqueous Tris as buffer A, 5 M NaBr as buffer B; a linear gradient from 0 to 30% B in 25 minutes) and capillary electrophoresis (CE) revealed coelution with authentic sample of dodecathymidyl thiophosphate.

D. Deprotection and Isolation of 24.

The solid support-bound 21 (FIG. 4) was treated with concentrated ammonia (5 mL) for 2 hours at room temperature, the solution was collected in a screw-cap vial and heated at 65° C. for 18 hours. After evaporation to dryness, the residue was dissolved in water (3 mL) and filtered. The 5'-DMTr protected oligonucleotide 23 was isolated by HPLC (DeltaPak 15 μ C18 300 Å, 3.9(300 mm; 0.1 M NH$_4$OAc as buffer A, 0.05 M NH$_4$OAc in 75% aqueous MeCN as buffer B; a linear gradient from 15 to 80% B in 30 minutes at a flow rate 5.0 mL min$^{-1}$). The collected fractions were evaporated, treated with 80% aqueous AcOH for 20 min, and evaporated to dryness. The residue was desalted on the same column eluting first with 0.1 M NaOAc (10 min), then with water (10 min) and finally eluting 24 as a sodium salt with 50% aqueous MeCN (20 min) at a flow rate 5.0 mL min$^{-1}$. Evaporation gave 634 OD (21.2 mg, 59.3 (Ci) of 24. Analysis by ion-exchange chromatography (Resource™ Q—1 mL column (Pharmacia); 0.02 M aqueous Tris as buffer A, 5 M NaBr as buffer B; a linear gradient from 0 to 30% B in 25 min) and capillary electrophoresis (CE) revealed coelution with authentic sample of dodecathymidyl thiophosphate. MALDI/TOF MS: found 3861.19; calculated for $C_{120}H_{158}N_{24}O_{73}P_{12}S_{12}$ 3861.14.

Example 11

Dodeca[(2-Pivaloylthio)ethyl 2'-O-(methoxyethyl)-5-methyluridyl phosphate] (25)

The title compound was assembled on an ABI 380B synthesizer by using 0.1 M (2-pivaloylthio)ethyl 5'-O-(4,4'-dimethoxytrityl)-2'-O-(2-methoxyethyl)-5-methylur idil N,N-diisopropylaminophosphite 2 in MeCN, 0.45 M 1H-tetrazole as an activator, 0.05 M (1S)-(+)-(10-camphorsulfonyl) oxaziridine in MeCN as an oxidizer, and 6 minute coupling time. Upon completion of the chain assembly (DMTr-Off synthesis) the solid support was dried on an oil pump, placed in a Pyrex test tube and suspended in 80% aqueous MeCN (3 mL). The suspension was degassed, placed in photochemical reactor, and irradiated for 30 minutes at room temperature. The tube was centrifuged, and supernatant was collected. A fresh portion of 80% aqueous MeCN was added. This procedure was repeated for 5 times until less than 4 OD of oligonucleotide material was released after irradiation for 30 minutes. The collected supernatants were diluted with water to yield a solution in 30% aqueous MeCN, applied on an HPLC column (DeltaPak 15μ C18 300 A, 3.9*300 mm), and chromatographed in a linear gradient from 25 to 80% MeCN in water for 40 minutes. The main peak was collected and evaporated in vacuo to afford the title compound in 25% yield.

An aliquot (5 OD) of the obtained material was treated with concentrated aqueous ammonia (2 mL) for 8 hours at room temperature, evaporated to dryness, and re-dissolved in water (200 μL). Analysis by capillary electrophoresis (CE) revealed comigration with authentic sample of dodeca [2'-O-(2-methoxyethyl)-5-methyluridyl phosphate]. ES MS: found 4557.45, calculated for $C_{156}H_{230}N_{24}O_{109}P_{12}$ 4557.26.

Example 12

Dodeca [(2-Pivaloylthio)ethyl 2'-O-(2-methoxyethyl)-5-methyluridyl thiophosphate] (26)

The title compound was prepared as described above except that 3H-1,2-benzodithiol-3-one 1,1-dioxide (0.05 M in MeCN) was used in an oxidation step as a sulfur transfer reagent. Chromatography on the same column in a linear gradient from 70 to 100% MeCN in water afforded the title compound in 15% yield. After treatment with concentrated aqueous ammonia as above, analysis by capillary electrophoresis (CE) revealed comigration with authentic sample of dodeca [2'-O-(2-methoxyethyl)-5-methyluridyl thiophosphate]. ES MS: found 4750.49, calculated for $C_{156}H_{230}N_{24}O_{97}P_{12}S_{12}$ 4750.10.

Analysis/Bioanalysis of SATE Oligomers

Mass analysis of SATE oligonucleotides was carried out using a MALDI-TOF mass spectrometer. Reversed phase HPLC analysis was also used to characterize the radiochemical purity of SATE oligomers. Preliminary results indicated that the extent of SATE removal can be analyzed using either reversed phase chromatography or MALDI-TOF. An oligonucleotide containing from 12 to 0 SATE groups was analyzed using a Zorbax C3 column using a buffer of 20 mM ammonium acetate. Elution was accomplished with an acetonitrile gradient. Fractions were collected and subjected to MALDI analysis confirming the mass identity of the peaks observed. Matrix formulation was a 1:1 mixture of a saturated solution of Tri-hydroxyacetophenone in 50/50 ACN/H$_2$O, and 0.2 M di-aminohydrogen citrate in 50/50 ACN/H$_2$O. Sample (1 μL) was mixed with matrix (5 μL) and this mixture (1 μL) was used for negative mode MALDI analysis.

Extraction methods for fully modified SATE oligomers and for oligomers that have lost one or more SATE groups will be developed for these analytical methods. These extraction methods will include both solid phase and phenol chloroform extraction protocols. Preliminary results indicate that a fully modified SATE oligomer can be isolated in a 80%–90% yield from tissue homogenates.

Treatment of SATE oligomers with ammonium hydroxide results in the loss of the SATE groups, leaving a phosphorothioate internucleotide linkage. Using methods established in our laboratory (See, Leeds, et al., *Anal. Biochem.* 1996, 235, 36; Crooke, et al., *J. Pharmacol. Exp. Ther.* 1996, 277(2), 923), analysis of these phosphorothioates will be accomplished using either Capillary Gel Electrophoresis (CGE) with UV detection, or using strong anion exchange chromatography with detection by UV or by fraction collection and scintillation counting. Briefly, oligonucleotides are isolated from homogenized tissue samples by treatment with proteinase K, followed by phenol/chloroform extraction, then solid phase extraction using anion exchange purification followed by reversed phase desalting of the isolated oligonucleotides and metabolites, followed by CGE analysis. For anion exchange chromatography with scintillation counting, the extracted oligonucleotides are analyzed after the phenol/chloroform step. Both methods will allow discrimination between full-length oligomers and metabolic degradation products.

Those skilled in the art will appreciate that numerous changes and modifications may be made to the preferred embodiments of the invention and that such changes and modifications may be made without departing from the spirit of the invention. It is therefore intended that the appended claims cover all such equivalent variations as fall within the true spirit and scope of the invention.

What is claimed is:

1. A method for preparing an oligomeric compound comprising a moiety having the Formula I:

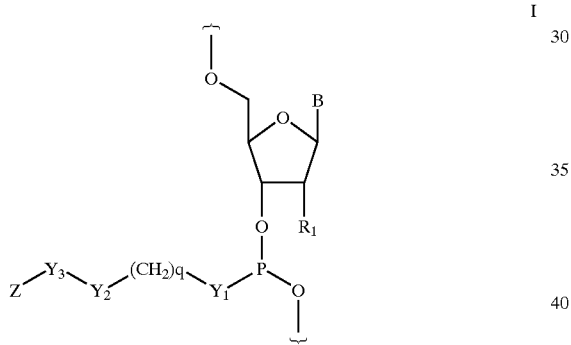

wherein $(CH_2)_q$—$Y_2$—$Y_3$—Z is a protecting group:

Z is aryl having 6 to about 14 carbon atoms or alkyl having from one to about six carbon atoms;

$Y_1$ is O or S;

$Y_2$ is O or S;

$Y_3$ is C(=O) or S;

q is 2 to about 4;

$R_1$ is H, OH, F, or a group of formula $R_7$—$(R_8)_n$;

$R_7$ is $C_3$–$C_{20}$ alkylene, $C_4$–$C_{20}$ alkenylene, $C_2$–$C_{20}$ alkynylene, $C_1$–$C_{20}$ alkoxy diradical, $C_2$–$C_{20}$ alkenyloxy diradical, or $C_2$–$C_{20}$ alkynyloxy diradical;

$R_8$ is hydrogen, amino, protected amino, halogen, hydroxyl, thiol, keto, carboxyl, nitro, nitroso, nitrile, trifluoromethyl, trifluoromethoxy, O-alkyl, S-alkyl, NH-alkyl, N-dialkyl, O-aryl, S-aryl, NH-aryl, O-aralkyl, S-aralkyl, NH-aralkyl, N-phthalimido, imidazolyl, azido, hydrazino, hydroxylamino, isocyanato, sulfhydryl, sulfo, disulfhydryl, sulfeno, aryl, heterocycle, carbocycle, intercalator, reporter molecule, conjugate, polyamine, polyamide, polyalkylene glycol, polyether, or a group of formula (—O—$X_3$)$_p$, where p is 2 to about 10 and $X_3$ is alkyl or alkylene having from one to about 10 carbons;

B is a naturally occurring or non-naturally occurring nucleobase that is optionally protected and optionally radiolabeled;

comprising the steps of:

providing a compound having the Formula II:

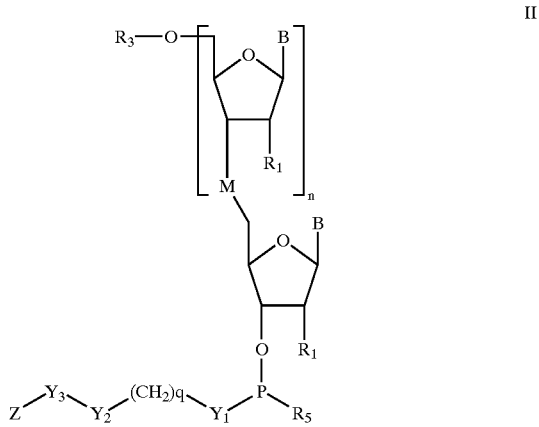

wherein:

$R_3$ is hydrogen, a hydroxyl protecting group, or a linker connected to a solid support;

M is an optionally protected internucleotide linkage;

each B, independently is a naturally occurring or non-naturally occurring nucleobase that is optionally protected and optionally radiolabeled;

n is 0 to about 50;

$R_5$ is —$N(R_6)_2$, or a heterocycloalkyl or heterocycloalkenyl ring containing from 4 to 7 atoms and up to 3 heteroatoms selected from the group consisting of nitrogen, sulfur, and oxygen;

$R_6$ is straight or branched chain alkyl having from 1 to 10 carbons;

reacting the compound of Formula II with a compound having Formula III:

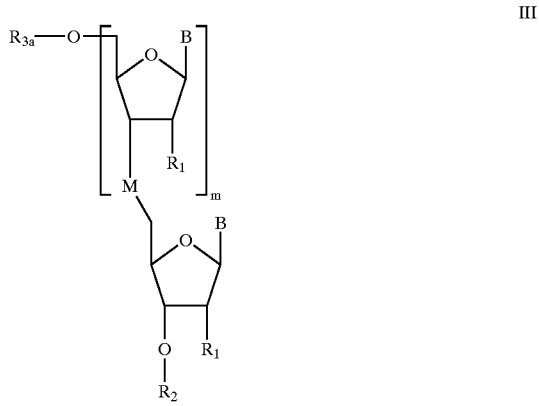

wherein:

$R_{3a}$ is hydrogen;

m is 0 to about 50;

$R_2$ is a hydroxyl protecting group, or a linker connected to a solid support, provided that $R_2$ and $R_3$ are not both simultaneously a linker connected to a solid support;

thereby forming the oligomeric compound; wherein the method further comprises cleaving said $(CH_2)_q$—$Y_2$—$Y_3$—Z group with base; and the compound of Formula II is formed by reaction of a compound having Formula V:

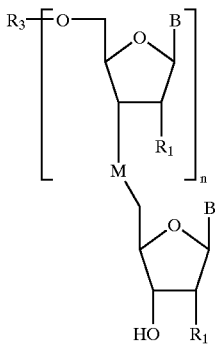

V with a compound having the Formula VI:

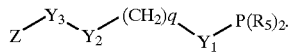

VI wherein B is a radiolabeled nucleobase.

2. The method of claim 1 further comprising the step of oxidizing or sulfurizing the oligomeric compound to form a compound having Formula III, wherein $R_{3a}$ is hydrogen, a hydroxyl protecting group, or a linker connected to a solid support; and where m is increased by n+1.

3. The method of claim 2 further comprising a capping step.

4. The method of claim 3 wherein the capping step is performed prior to oxidation.

5. The method of claim 1 wherein q is 2; and $Y_3$ is C(=O).

6. The method of claim 1 wherein Z is methyl, phenyl or t-butyl.

7. The method of claim 6 wherein Z is t-butyl.

8. The method of claim 5 wherein n is 0.

9. The method of claim 5 wherein $R_2$ is a linker to a solid support.

10. The method of claim 5 wherein $Y_1$ and $Y_2$ are each O.

11. The method of claim 5 wherein $Y_1$ and $Y_2$ are each S.

12. The method of claim 5 wherein $Y_1$ is O and $Y_2$ is S.

13. The method of claim 5 wherein each $R_6$ is isopropyl.

14. The method of claim 5 wherein n is 0; $R_3$ is H, $R_5$ is diisopropylamino; $Y_1$ is O; $Y_2$ is S; and Z is methyl or t-butyl.

15. The method of claim 14 wherein Z is t-butyl.

16. The method of claim 1 wherein the radiolabeled nucleobase has the formula:

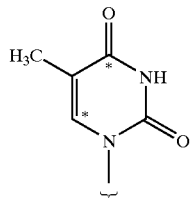

wherein denotes a $^{14}C$ atom.

17. The method of claim 14 wherein B is a radiolabeled nucleobase of formula:

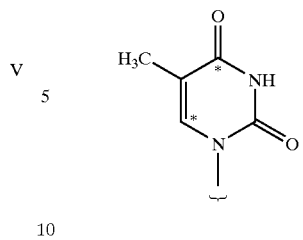

wherein denotes a $^{14}C$ atom.

18. The method of claim 1 wherein N is an optionally protected phosphodiester, phosphorothioate, phosphorodithioate, or alkyl phosphonate internucleotide linkage.

19. A method for preparing an oligomeric compound comprising a moiety having the Formula I:

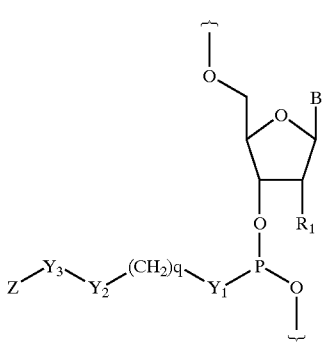

I wherein $(CH_2)_q$—$Y_2$—$Y_3$—Z is a protecting group:

Z is aryl having 6 to about 14 carbon atoms or alkyl having from one to about six carbon atoms;

$Y_1$ is O or S;

$Y_2$ is O or S;

$Y_3$ is C(=O) or S;

q is 2 to about 4;

$R_1$ is H, OH, F, or a group of formula $R_7$—$(R_8)_n$;

$R_7$ is $C_3$–$C_{20}$ alkylene, $C_4$–$C_{20}$ alkenylene, $C_2$–$C_{20}$ alkynylene, $C_1$–$C_{20}$ alkoxy diradical, $C_2$–$C_{20}$ alkenyloxy diradical, or $C_2$–$C_{20}$ alkynyloxy diradical;

$R_8$ is hydrogen, amino, protected amino, halogen, hydroxyl, thiol, keto, carboxyl, nitro, nitroso, nitrile, trifluoromethyl, trifluoromethoxy, O-alkyl, S-alkyl, NH-alkyl, N-dialkyl, O-aryl, S-aryl, NH-aryl, O-aralkyl, S-aralkyl, NH-aralkyl, N-phthalimido, imidazolyl, azido, hydrazino, hydroxylamino, isocyanato, sulfhydryl, sulfo, disulfhydryl, sulfeno, aryl, heterocycle, carbocycle, intercalator, reporter molecule, conjugate, polyamine, polyamide, polyalkylene glycol, polyether, or a group of formula (—O—$X_3)_p$, where p is 2 to about 10 and $X_3$ is alkyl or alkylene having from one to about 10 carbons;

B is a naturally occurring or non-naturally occurring nucleobase that is optionally protected and optionally radiolabeled;

comprising the steps of:

providing a compound having the Formula II:

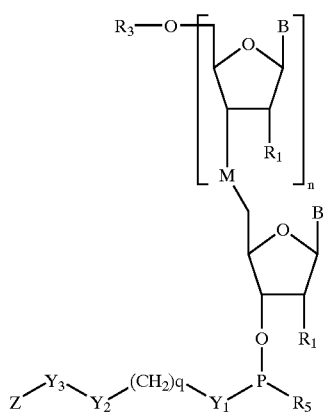

wherein:
$R_3$ is hydrogen, a hydroxyl protecting group, or a linker connected to a solid support;
M is an optionally protected internucleotide linkage;
each B, independently is a naturally occurring or non-naturally occurring nucleobase that is optionally protected and optionally radiolabeled;
n is 0 to about 50;
$R_5$ is $-N(R_6)_2$, or a heterocycloalkyl or heterocycloalkenyl ring containing from 4 to 7 atoms and up to 3 heteroatoms selected from nitrogen, sulfur, and oxygen;
$R_6$ is straight or branched chain alkyl having from 1 to 10 carbons;
reacting the compound of Formula II with a compound having Formula III:

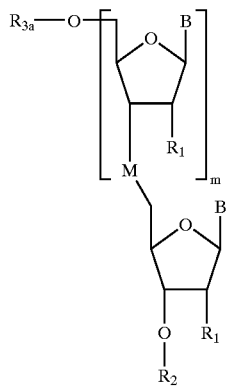

wherein:

$R_{3a}$ is hydrogen;
m is 0 to about 50;
$R_2$ is a hydroxyl protecting group, or a linker connected to a solid support, provided that $R_2$ and $R_3$ are not both simultaneously a linker connected to a solid support;

thereby forming the oligomeric compound; wherein the compound of Formula II is formed by:

reacting a compound having Formula:

wherein X is a halogen;
with a compound of Formula:

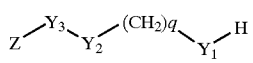

in the presence of an acid to form a compound of Formula VI:

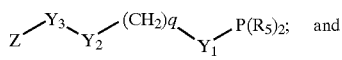

reacting the compound of Formula VI with a compound of Formula V:

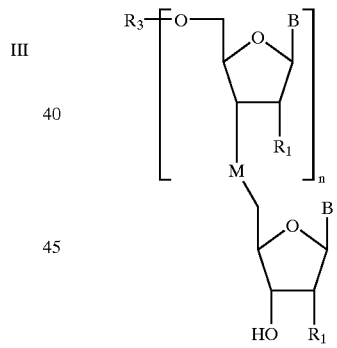

in the presence of an acid.

* * * * *

UNITED STATES PATENT AND TRADEMARK OFFICE
CERTIFICATE OF CORRECTION

PATENT NO. : 6,531,590 B1
DATED : March 11, 2003
INVENTOR(S) : Muthiah Manoharan et al.

It is certified that error appears in the above-identified patent and that said Letters Patent is hereby corrected as shown below:

Column 7,
Line 30, please delete "Y2" and insert therefor -- $Y_2$ --;

Column 8,
Line 53, please delete "Phosphorordiamidite" and insert therefor -- Phosphorodiamidite --;

Column 9,
Line 25, please delete "z" and insert therefor -- Z --;

Column 11,
Line 18, please insert -- * -- between "wherein" and "denotes";

Column 31,
Line 65, after "wherein" please insert -- * --;

Column 32,
Line 14, please delete "N" and insert therefor -- M --;
Line 12, after "wherein" please insert -- * --.

Signed and Sealed this

Eighth Day of June, 2004

JON W. DUDAS
*Acting Director of the United States Patent and Trademark Office*